US011676125B2

(12) United States Patent
Mimassi

(10) Patent No.: US 11,676,125 B2
(45) **Date of Patent: *Jun. 13, 2023**

(54) SYSTEM AND METHOD FOR THIRD-PARTY FOOD AND DINING ORDERING CONTROL

(71) Applicant: RockSpoon, Inc., San Jose, CA (US)

(72) Inventor: Nagib Georges Mimassi, Palo Alto, CA (US)

(73) Assignee: ROCKSPOON, INC., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/734,055

(22) Filed: Apr. 30, 2022

(65) Prior Publication Data

US 2022/0335404 A1 Oct. 20, 2022

Related U.S. Application Data

(63) Continuation of application No. 17/571,515, filed on Jan. 9, 2022, now Pat. No. 11,403,611, which is a continuation of application No. 17/005,038, filed on Aug. 27, 2020, now Pat. No. 11,232,426, which is a continuation-in-part of application No. 16/796,342, filed on Feb. 20, 2020, now Pat. No. 10,803,442.

(60) Provisional application No. 62/964,413, filed on Jan. 22, 2020, provisional application No. 62/938,817, filed on Nov. 21, 2019.

(51) Int. Cl.

| | |
|---|---|
| ***G06Q 20/22*** | (2012.01) |
| ***G06Q 20/40*** | (2012.01) |
| ***G16H 20/60*** | (2018.01) |
| ***G06Q 50/12*** | (2012.01) |

(52) U.S. Cl.

CPC ... *G06Q 20/2295* (2020.05); *G06Q 20/40145* (2013.01); *G06Q 50/12* (2013.01); *G16H 20/60* (2018.01)

(58) Field of Classification Search

CPC .................................................. G06Q 20/2295
USPC .................................................. 705/35–45
See application file for complete search history.

(56) References Cited

U.S. PATENT DOCUMENTS

| | | | | |
|---|---|---|---|---|
| 2005/0125321 A1* | 6/2005 | Gerstner | G06Q 20/385 | 705/42 |
| 2007/0063017 A1* | 3/2007 | Chen | G06Q 20/40 | 235/379 |
| 2009/0106158 A1* | 4/2009 | Hill | G06Q 20/10 | 705/41 |

(Continued)

*Primary Examiner* — Robert R Niquette

(74) *Attorney, Agent, or Firm* — Galvin Patent Law LLC; Brian R. Galvin

(57) ABSTRACT

A system and method for third-party food and dining ordering control, comprising at least one device capable of accessing the internet which may be a mobile device or personal computing device such as a laptop or desktop, a web application, and a point-of-sale system at a restaurant or retailer, wherein users of the web application may deposit funds into an account and set regulations on what they may purchase with the deposited funds, or have an administrator set up an account for them such as a parent setting up an account for a child or a doctor setting up an account for a patient, allowing the parent or doctor or other administrator to regulate what the sub-user such as the child or patient may purchase, in keeping with budget, diet, and lifestyle restrictions, and which may utilize zero-step authentication to allow for seamless use of the service at certain establishments.

20 Claims, 20 Drawing Sheets

(56) References Cited

U.S. PATENT DOCUMENTS

| | | | | |
|---|---|---|---|---|
| 2009/0327114 | A1* | 12/2009 | Sheth | G07F 7/1041 705/35 |
| 2013/0159119 | A1* | 6/2013 | Henderson | G06Q 30/0185 705/41 |
| 2014/0214640 | A1* | 7/2014 | Mallikarjunan | G06Q 20/322 705/35 |

* cited by examiner

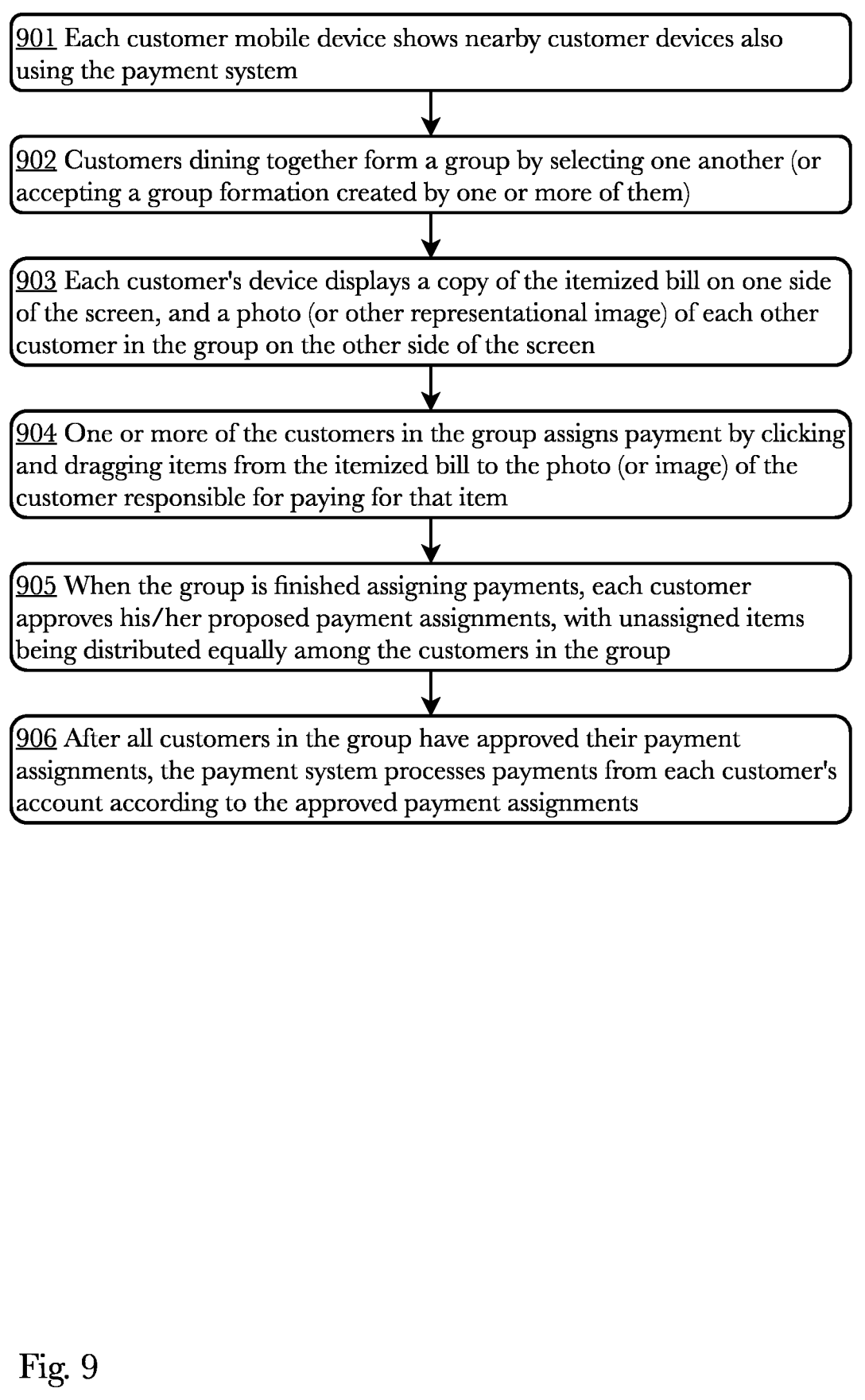

901 Each customer mobile device shows nearby customer devices also using the payment system

↓

902 Customers dining together form a group by selecting one another (or accepting a group formation created by one or more of them)

↓

903 Each customer's device displays a copy of the itemized bill on one side of the screen, and a photo (or other representational image) of each other customer in the group on the other side of the screen

↓

904 One or more of the customers in the group assigns payment by clicking and dragging items from the itemized bill to the photo (or image) of the customer responsible for paying for that item

↓

905 When the group is finished assigning payments, each customer approves his/her proposed payment assignments, with unassigned items being distributed equally among the customers in the group

↓

906 After all customers in the group have approved their payment assignments, the payment system processes payments from each customer's account according to the approved payment assignments

Fig. 9

SYSTEM AND METHOD FOR THIRD-PARTY FOOD AND DINING ORDERING CONTROL

CROSS-REFERENCE TO RELATED APPLICATIONS

Priority is claimed in the application data sheet to the following patents or patent applications, the entire written description of each of which is expressly incorporated herein by reference in its entirety:

Ser. No. 17/571,515
Ser. No. 17/005,038
Ser. No. 16/796,342
62/938,817
62/964,413

BACKGROUND

Field of the Art

The disclosure relates to the field of payment systems, and more particularly to the field of third-party and self regulated online payment services and integration with restaurants and retailers.

Discussion of the State of the Art

The advent of online payments and the ease of setting up online payment accounts, and the ease of transferring funds online between banking and other financial institutions, has benefited society in many ways, allowing for easy transfer of funds between individuals online and easy payment for goods without ever having actual, physical dollar bills or other physical currency involved. It is possible for family members to transfer funds to the accounts of other family members quite easily, and for parents to support their children with funds such as when they are in university or when they have an allowance on their own debit card or with an online account. This, however, comes with many risks, of the child, or other individual including an independent user of online finances and banking, to misuse their funds, and to purchase unhealthy, dangerous, or expensive and unneeded goods, due to a lack of self control and the ease with which one can transfer funds and make purchases with online banking and even online shopping.

There exists no easy way for parents to control what their child can spend money on or to help guide them to healthier lifestyles, and likewise it is common for people who attempt to self-regulate their diets and lifestyles in accordance with personal goals, doctor recommendations, or dietician and nutritionist recommendations, to fall short of their goals and purchase unhealthy or unneeded goods. No system of keeping track of dietary or budgeting or lifestyle constraints currently integrates with point-of-sale systems in a similar way that online financing and banking already does, either, resulting in an extremely easy method to acquire goods detrimental to one's health or lifestyle or budget, but no easy way to control such purchases if one lacks the (sometimes immense) self control to prevent such purchases in the first place. This is made even harder for individuals with actual disabilities or deficiencies which make responsible purchasing more difficult, such as those suffering from depression or complex dietary restrictions which they struggle to meet.

SUMMARY

Accordingly, the inventor has conceived and reduced to practice, a system and method for third-party food and dining ordering control, comprising at least one device capable of accessing the internet which may be a mobile device or personal computing device such as a laptop or desktop, a web application, and a point-of-sale system at a restaurant or retailer, wherein users of the web application may deposit funds into an account and set regulations on what they may purchase with the deposited funds, or have an administrator set up an account for them such as a parent setting up an account for a child or a doctor setting up an account for a patient, allowing the parent or doctor or other administrator to regulate what the sub-user such as the child or patient may purchase, in keeping with budget, diet, and lifestyle restrictions, and which may utilize zero-step authentication to allow for seamless use of the service at certain establishments.

According to a preferred embodiment, a system for third-party food and dining ordering control is disclosed, comprising: at least one computer capable of communicating over the Internet; at least one point of sale system; a datastore; a web application comprising a first memory, a first processor, and a first plurality of programming instructions stored in the first memory, and operating on the first processor, wherein the first plurality of programming instructions, when operating on the processor, cause the web application to: facilitate two-way communications with the at least one computer capable of communicating over the Internet and the application; facilitate two-way communications with the at least one point of sale system and the application; allow users of the at least one computer capable of communicating over the Internet to provide account registration data with the application; wherein the data received from users may be encrypted; store the registration data in the datastore; allow registered users to deposit funds into their account data; allow users to specify other subordinate users to their account; wherein the registered user and the specified subordinate users may use the stored funds to make purchases of food at restaurants and retailers; wherein the restaurants and retailers at which purchases may be made, and the types of p purchases that may be made, are specified by the registered user; allow for the registered user to specify any third parties to notify of attempted purchases using stored funds; and notify specified third parties, if any, of any attempted purchases using stored funds.

According to another preferred embodiment, a method for third-party food and dining ordering control is disclosed, comprising the steps of: facilitating two-way communications with the at least one computer capable of communicating over the Internet and the application, using a web application and at least one computer capable of communicating over the Internet; facilitating two-way communications with the at least one point of sale system and the application, using a web application and at least one point of sale system; allowing users of the at least one computer capable of communicating over the Internet to provide account registration data with the application, using a web application and at least one computer capable of communicating over the Internet; wherein the data received from users may be encrypted; storing the registration data in the datastore, using a web application and datastore; allowing registered users to deposit funds into their account data, using a web application and datastore; allowing users to specify other subordinate users to their account, using a web application and at least one computer capable of communicating over the Internet; wherein the registered user and the specified subordinate users may use the stored funds to make purchases of food at restaurants and retailers; wherein the restaurants and retailers at which purchases may be made, and the types of p purchases that may be made, are specified by the registered user; allowing for the registered user to specify any third parties to notify of attempted purchases using stored funds, using a web application and at least one computer capable of communicating over the Internet; and notifying third parties of any attempted purchases using stored funds, using a web application.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 9 is a flow diagram showing the steps of an exemplary method for bill splitting among customers.

DETAILED DESCRIPTION

Figure 1:
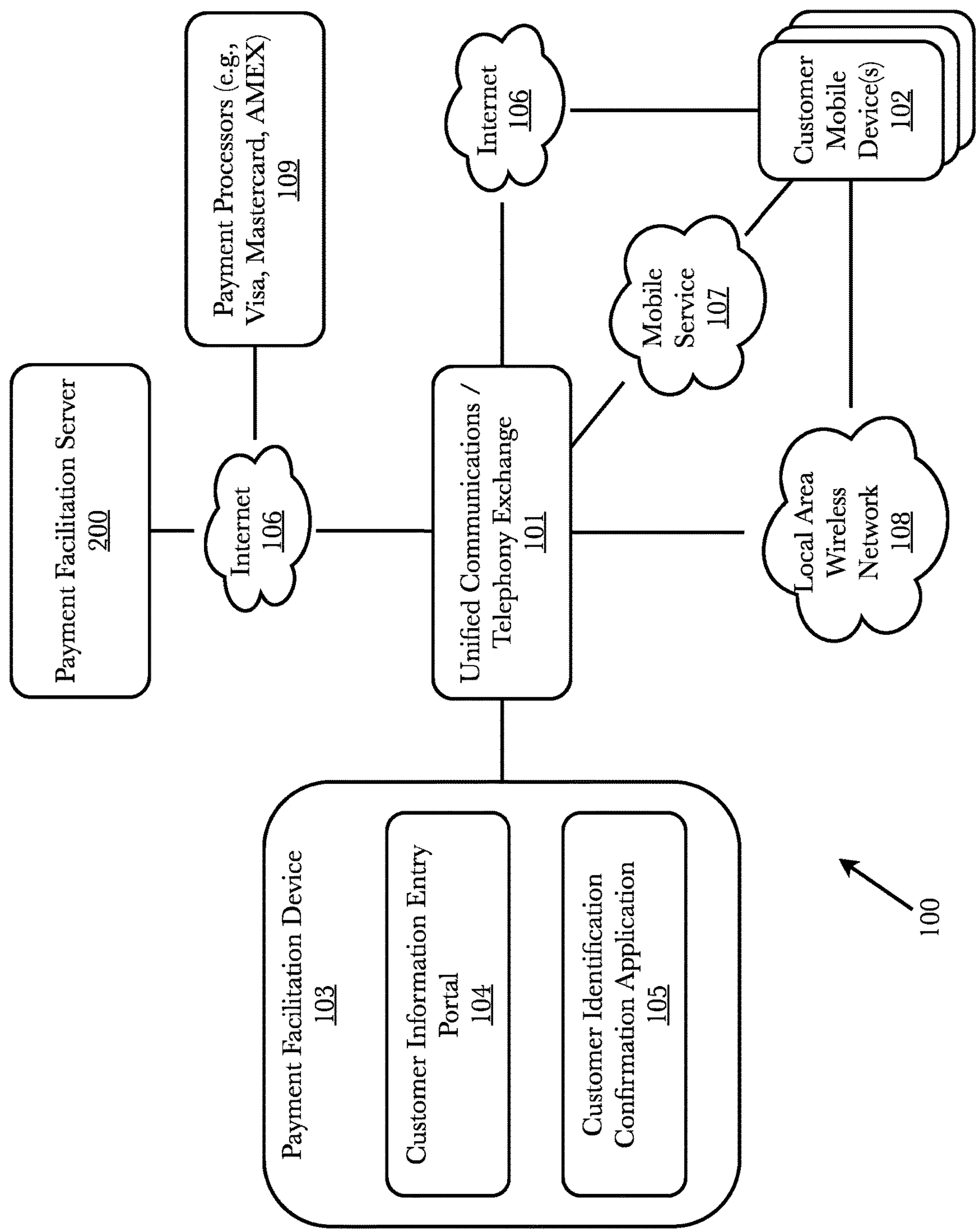
FIG. 1 is a block diagram illustrating an exemplary system architecture for a zero-step authentication system.

The inventor has conceived, and reduced to practice, a zero-step authentication system and method which uses wireless mobile devices to automatically make payments in a secure manner without requiring the customer to handle his or her mobile device. The system and method uses a payment facilitation device at the business location which automatically detects and recognizes registered mobile devices, displays a photo of the customer to a business employee for identity confirmation, and automatically deducts payments for purchases from a pre-authorized customer account. The customer account is managed by a payment processing server, which stores the customer account data, makes appropriate deductions, sends confirmation of deductions to the customer's mobile device, and automatically refills the customer's account by making pre-authorized charges to the customer's banking institution.

Because the customer does not have to focus on his or her mobile device, the customer is free to interact naturally with the business environment and with employees of the business. For example, the customer is free to look around to experience the store's ambiance, which will tend to create a positive impression on the customer, and increase the likelihood that the customer will wish to return. Further, the customer is free to look at and speak with the business' employees, which facilitates personal interactions and relationships, making the customer feel more welcome and also increasing the likelihood that the customer will wish to return. These natural interactions are hindered by the handling and use of mobile phones, where the customer's attention is drawn away from the business environment and its employees in order to focus on the details of making or approving the transaction using his or her mobile device.

While the examples herein primarily discuss authorization of payments, the invention is not limited to authorization of monetary transactions, and can be used for authorization and transfer of any asset, or representation of an asset, that can be transferred electronically, for example: electronic transfers of real currency (credit card charges, bank transfers and payments, etc.), transfers of blockchain-based currencies such as Bitcoin, and transfers of digitized contracts or promises to pay or transfer physical assets (including, but not limited to, IOUs, certificates of ownership of stocks or other securities, and deeds for real estate).

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Definitions

"Business establishment" or "place of business" as used herein mean the location of any business entity with which customers may transact business. Typically, this will be a physical location where customers may enter the location and transact business directly with employees of the business, but may also be a business without a physical location such as an online or telephone order retailer. Many examples herein use a restaurant as the business establishment, but the invention is not limited to use in restaurants, and is applicable to any business establishment.

The term "network" as used herein means any communication connection between two or more computing devices, whether such connection is made directly (e.g., from one device containing a Bluetooth radio to another device containing a Bluetooth radio) or through an intermediary device such as a router, where a number of devices connected to the router may all communicate with one another.

Conceptual Architecture

FIG. 1 is a block diagram illustrating an exemplary system architecture 100 for a zero-step authentication system. The primary components of the system are a payment facilitation device 103, a unified communications device or telephony exchange system (UC system) 101, and a payment facilitation server 200. Components or services that may connect to or be accessed by the system include wireless customer mobile devices 102, and payment processors 109. The payment facilitation device 103 is a computing device located at a business establishment that is connected (wired or wirelessly) to a UC system 101. The payment facilitation device 103 may be wired, or wireless, or both, depending on the implementation of a given embodiment. While a payment facilitation device 103 and UC system 101 are specified in this embodiment, it is not required that they be precisely in this configuration, and other configurations are possible, including a non-SIP computing device connected to a network without a UC system 101. The payment facilitation device 103 comprises a screen (not shown) and applications for a customer information entry portal 104 and a customer identification confirmation application 105. The payment facilitation device 103 may be a mobile computing device like a mobile phone or tablet computer or may be a desktop or tabletop computing device.

The customer information entry portal 104 is an application on the payment facilitation device 103 that allows an employee of the business to enter customer details such as name, telephone number, device identifier, bank, debit, or credit card details, payment preferences, and, if necessary, customer account refill limits and customer account refill amounts. The device identifier may be any information that allows the system to identify the customer mobile device 102, including, but not limited to, a mobile access control (MAC) address (e.g., a MAC address for the device's WiFi radio, a MAC address for the device's Bluetooth radio, etc.), the device's 102 serial number, the device's mobile equipment identifier (MEID) or international mobile equipment identity (IMEI) number, the integrated circuit card identifier (ICCID) of the subscriber identity module (SIM) card inserted into the customer mobile device 102, and the device's 102 secure element identification (SEID) number.

The customer identification and confirmation application 105 is an application that provides security in financial transactions by allowing the employee of the business to visually confirm the identity of the customer making a transaction. For example, the payment facilitation device at a particular business location may be connected to multiple customer devices simultaneously. The customer identification and confirmation application 105 may display a photo of the user (customer) of each such connected customer device, and the employee may select the device of the customer making the transaction by clicking on the customer's photo as displayed by the customer identification and confirmation application 105 on the payment facilitation device 103.

The UC system 101 is a device or service (e.g., online service) that integrates different methods of communication (e.g., phone calls, video calls, short message service (SMS), instant messaging (chat), email) and allows for all of those different methods of communication to be accessed through a computing device such as a mobile phone or tablet computer. A UC system 101 is the modern, and much more flexible and powerful, form of a private branch exchange (PBX) telephone equipment system that allowed businesses to connect multiple internal telephones to a single incoming telephone line. In this example, the UC system 101 acts as the interface between the payment facilitation device 103, the customer mobile devices 102, and the payment facilitation server 200.

A customer mobile device 102 may be connected to the system via any wireless network connection, for example through the Internet 106, a mobile (cellular) network 107, or through a local wireless network 108 such as WiFI, Bluetooth, etc. In the case of remote connections such as those made through the Internet 106 or mobile service 107, the location of a customer mobile device 102 and its location relative to the payment facilitation device 103 or other customer mobile devices 102 may be established through use of the device's satellite positioning system hardware (e.g., GPS, GLONASS, Galileo), by identifying the location of an intermediary device to which the device is connected (e.g., a WiFi router, etc. In the case of local connections, which typically use short range wireless transmissions, it may not be necessary to determine the location of the mobile customer device 102 because the short range of wireless communications establishes that the payment facilitation device 103 or other mobile customer devices are nearby. For example, when using a Bluetooth Class 2 connection to connect to other devices, it will be apparent that the other devices are nearby because Bluetooth Class 2 has an effective range on the order of 10 meters.

In a typical scenario, the first time a customer enters a business establishment with a customer mobile device 102, an employee of the business establishment will enter the customer's information using the customer information entry portal 104 and register the customer mobile device 102 using the customer mobile device's 102 identification. When a customer mobile device 102 enters a business establishment, the payment facilitation device 103 and customer mobile device 102 will automatically detect each other and establish a network connection. The payment facilitation device 103 will recognize the customer mobile device 102 using the customer mobile device's identifier. As the customer makes an order, the business's employee will confirm the identity of the customer using the customer identification confirmation application 105. The payment facilitation device connects to the payment facilitation server 200, either directly or through the UC system 101, forwards the customer information and order information to the payment facilitation server 200. The payment facilitation server 200, checks the customer's account and either deducts an appropriate amount from the customer's prepaid account or sends the payment details to a payment processor 109 for processing. Once the payment is processed, the payment facilitation server 200 sends a confirmation of the payment either to the payment facilitation device 103, the customer mobile device 102, or both. In a scenario where the customer is in a remote location from the business establishment (e.g., a phone order or online order), the process is much the same except that the first time customer information entry and mobile device registration occurs remotely, and the employee does not visually identify the customer (although other methods of identifying the customer may apply, such as personal identification number (PIN) codes, voice print identification, telephone number identification, or customer mobile device 102 identifiers).

Figure 2:
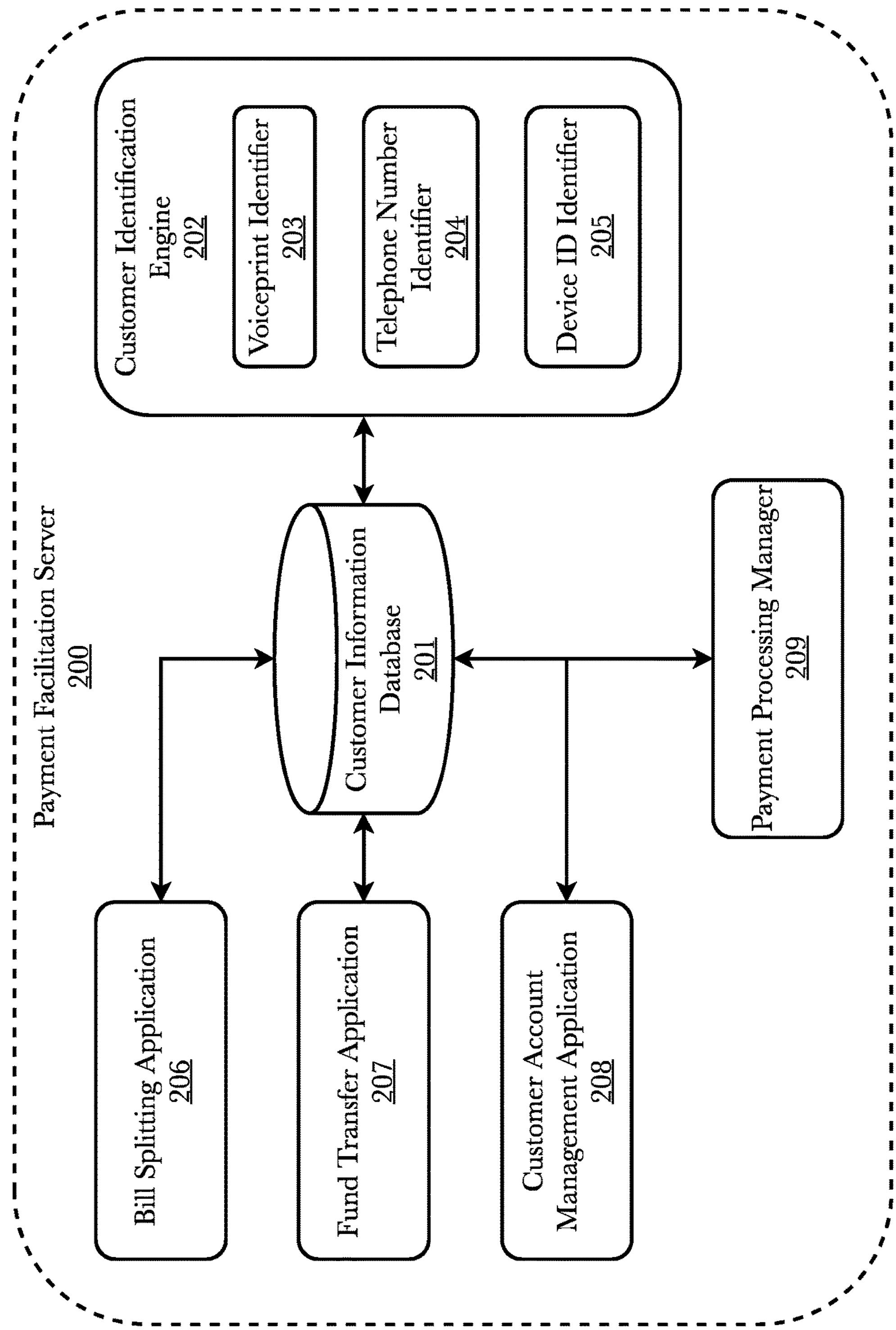
FIG. 2 is a block diagram illustrating an exemplary architecture for an aspect of zero-step authentication system, the payment facilitation server.

FIG. 2 is a block diagram illustrating an exemplary architecture for an aspect of zero-step authentication system, the payment facilitation server 200. The payment facilitation server 200 manages customer information and payments from multiple customers. In this example, the payment facilitation server comprises a customer information database 201, a customer identification engine 202, a payment processing manager 209, and one or more applications for managing bill splitting, fund transfers, and account information. Note that, in some embodiments, the bill splitting and fund transfer applications may be applications on the customer mobile device 102 instead of on the payment facilitation server 200. As the payment facilitation server receives customer information and device registrations, it stores them in a customer information database. Such customer information may comprise customer details such as name, telephone number, device identifier, bank, debit, or credit card details, payment preferences, and, if necessary, customer account refill limits and customer account refill amounts. The device identifier may be any information that allows the system to identify the customer mobile device 102, including, but not limited to, a mobile access control (MAC) address (e.g., a MAC address for the device's WiFi radio, a MAC address for the device's Bluetooth radio, etc.), the device's 102 serial number, the device's mobile equipment identifier (MEID) or international mobile equipment identity (IMEI) number, the integrated circuit card identifier (ICCID) of the subscriber identity module (SIM) card inserted into the customer mobile device 102, and the device's 102 secure element identification (SEID) number.

The customer identification engine 202 provides additional security by confirming the identity of the customer before processing payments. In this example, the customer identification engine 202 has three separate identification methods, a voiceprint identifier 203, a telephone number identifier 204, and a device ID identifier 205. The voiceprint identifier 203 can provide confirmations of customer identities either by matching voice samples of specific words and phrases provided by the customer during account creation and device registration or, in a more sophisticated version, may match the customer's voice to any spoken words and phrases using machine learning algorithms. The telephone number identifier 204 receives caller identification (caller ID) information from the UC system 101, and verifies that the phone number from which the order is being made matches the phone number in the customer account information. The device ID identifier 205 receives a device identifier from the UC system 101 and matches it to the device identifier in the customer database 201 to confirm that the device is registered. In some embodiments, other methods of identifying the customer may be used, for example, PIN codes. In some embodiments, two or more of these identifiers may be used together to confirm the customer's identity.

As customer information and order information is received, the payment facilitation server 200 checks the customer's account using the customer account management application 208 and either deducts and appropriate amount from the customer's prepaid account or sends the payment details to the payment processing manager 209, which forwards the payment request to a payment processor 109 for processing. Once the payment is processed, the payment facilitation server 200 sends a confirmation of the payment either to the payment facilitation device 103, the customer mobile device 102, or both.

The bill splitting application 206 receives a bill that is to be shared by two or more customers (e.g., a restaurant dining bill), the device identifier of two or more customer mobile devices 102, and provides an interface for those customers to allocate items on the bill between the customers. Once each of the customers involved approves the allocation, the bill splitting application forwards each customer's portion of the bill to the payment processing manager 209 The fund transfer application 207 operates in a similar manner for fund transfers between customers. Customers involved in the fund transfer specify amounts to be transferred to other customers, and once approved by all customers involved in the fund transfer, the fund transfer application forwards the approved fund transfers to the payment processing manager 209 for execution.

Figure 3:
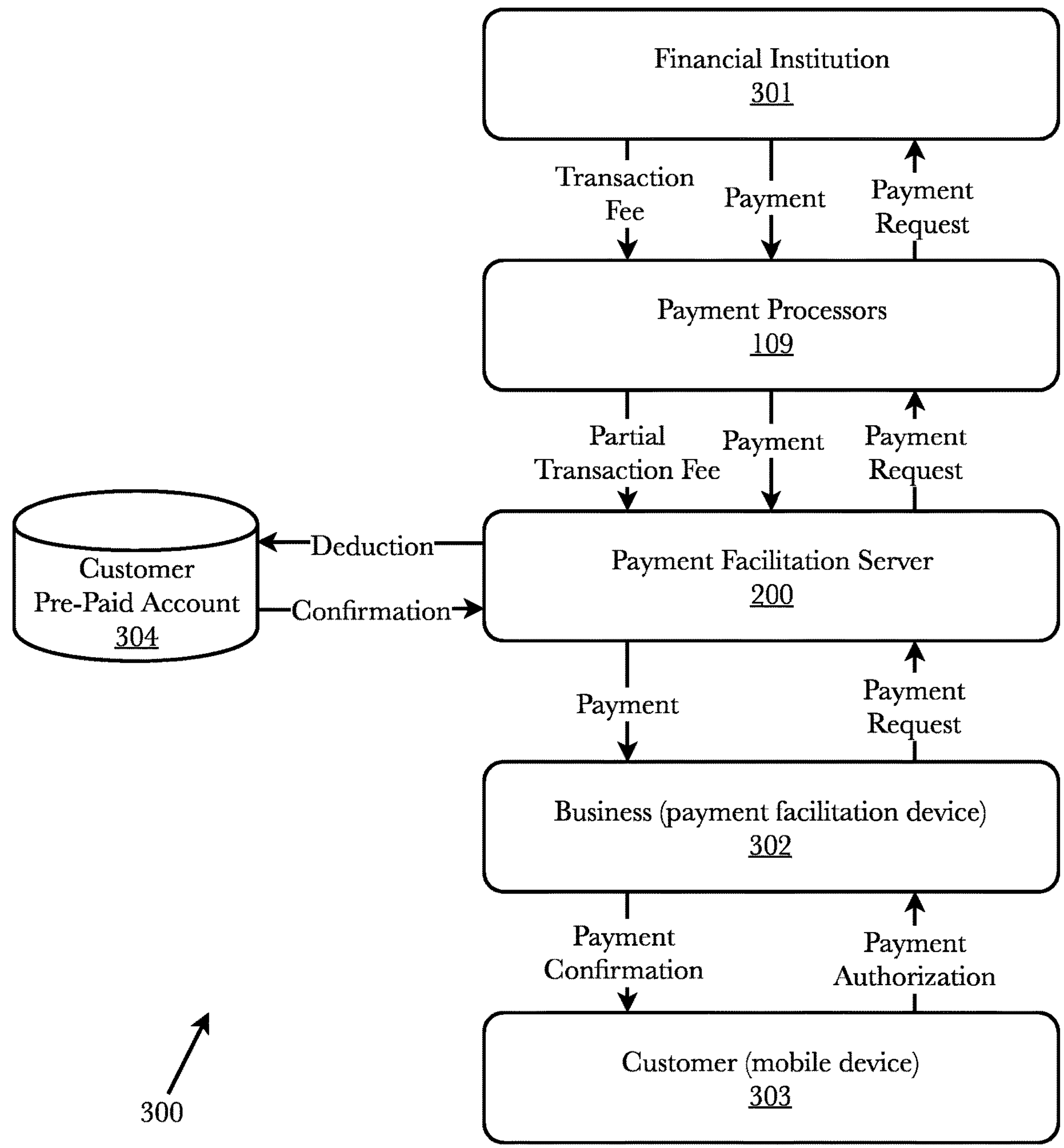
FIG. 3 is a flow diagram illustrating an exemplary flow of payments in an embodiment.

FIG. 3 is a flow diagram illustrating an exemplary flow of payments 300 in an embodiment. When a customer 303 authorizes a transaction (which authorization may be pre-approved) through his or her customer mobile device 102, the payment authorization is sent to the business 302 at the business' payment facilitation device 103. The payment facilitation device 103 of the business 302 sends a payment request to the payment facilitation server 200. The payment facilitation server 200 checks the customer's pre-paid account 304 to determine whether pre-paid funds are available. If such funds are available, a deduction is made from the customer pre-paid account 304 in the amount of the authorized payment, and a confirmation is confirmed by the payment facilitation server 200. If sufficient funds are not available in the customer pre-paid account, the account is either refilled or a direct payment request is made. In either case, the payment facilitation server 200 sends a payment request to a payment processor 109, which are financial intermediaries like Visa and Mastercard, who process transactions on behalf of financial institutions 301 (i.e., banks). The payment processor 109 sends the payment request to a financial institution 301 at which the customer 303 has an account. The financial institution 301 receives the payment request, and sends a payment to the payment processor 109, typically along with a transaction fee. The payment processor 109 receives the payment and transaction fee, and forwards the payment to the payment facilitation server along with a portion of the transaction fee. The payment facilitation server 200 forwards the payment to the business 302, which forwards a confirmation of payment 303 to the customer, completing the transaction.

Figure 15:
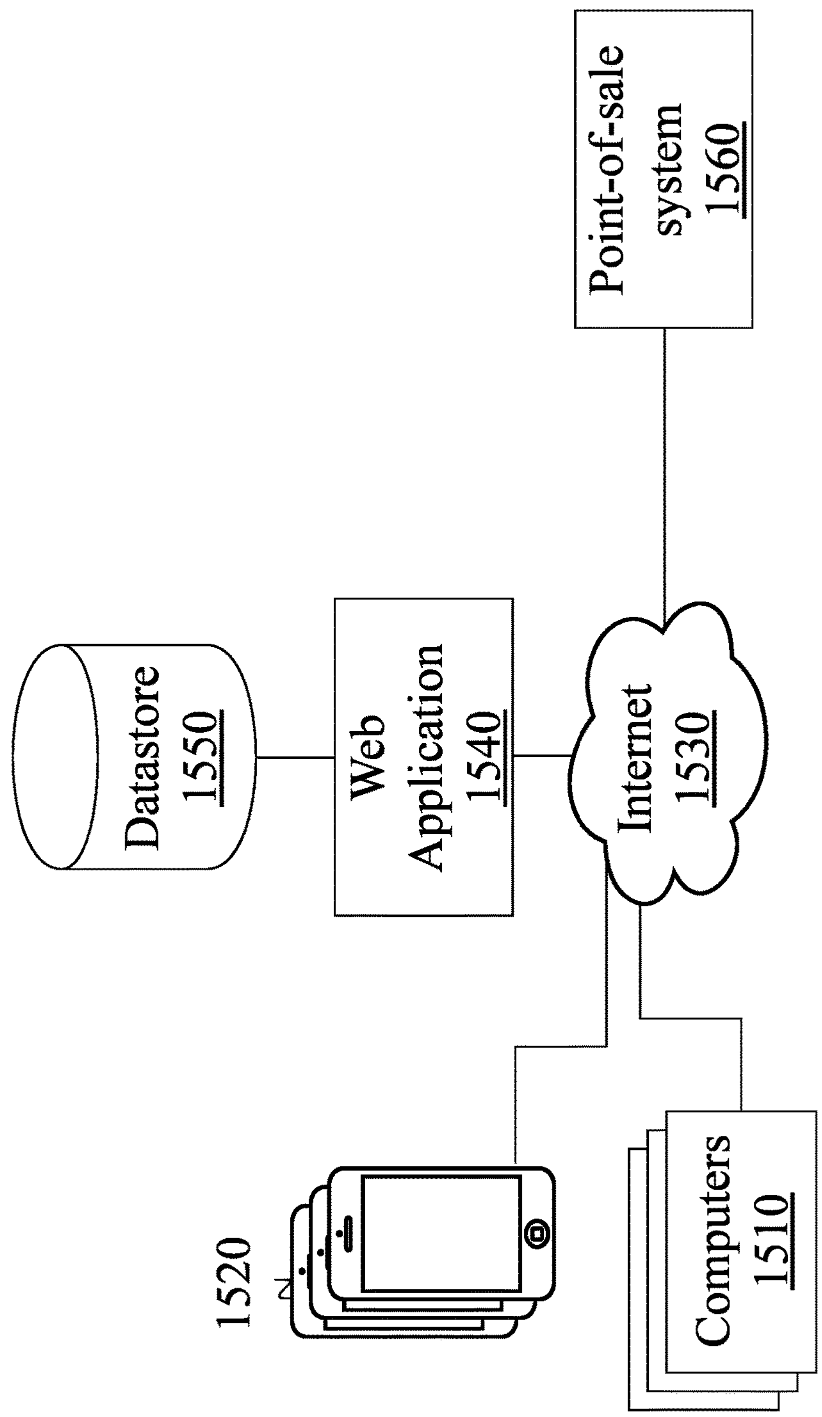
FIG. 15 is a system diagram of a system for third-party food and dining and retail purchase ordering control, according to an embodiment.

FIG. 15 is a system diagram of a system for third-party food and dining and retail purchase ordering control, according to an embodiment. A computer or computers 1510 exist, which may be separate and unconnected devices such as computers running in different buildings on different networks, such as a home computer, and a computer at a doctor's office. These computers may have at least an operating system and network adapter, and network connection, as well as associated hardware that allows such a computer to operate, such as volatile memory, a power source, and other common components for a computer. A mobile device or collection of mobile devices 1520 also may exist, including mobile phones, personal digital assistants or similar, and tablets, which may be able to communicate over a network, and may be owned and operated separately, rather than together on the same network or by the same user. The computer or computers 1510 and mobile device or devices 1520 all may communicate over the Internet 1530, with common protocols such as Hyper Text Transfer Protocol ("HTTP") and Transmission Control Protocol ("TCP"), to a web application 1540 using one of their supported protocols. A web application may be accessed through a website using HTTP communications, may be used through TCP communications with a specific application to operate as an interface between the computer and the application, and may use any of a variety of possible encryption or security features such as HTTP Secure or RSA encryption to protect user data. A datastore 1550 may exist either on the same server or servers as web application 1540, or on a network connection and accessed by web application 1540. A point-of-sale or "POS" system for a restaurant, store, or other vendor 1560 is also present, connected over the internet 1530 and communicating with a web application 1540. The POS 1560 may communicate over the Internet 1530 with web application 1540 with common protocols such as Hyper Text Transfer Protocol ("HTTP") or Transmission Control Protocol ("TCP"), using one of the supported protocols. Web application 1540 may be accessed through a website using HTTP communications, may be used through TCP communications with a specific application to operate as an interface between the computer and the application, and may use any of a variety of possible encryption or security features such as HTTP Secure or RSA encryption to protect user data.

Figure 16:
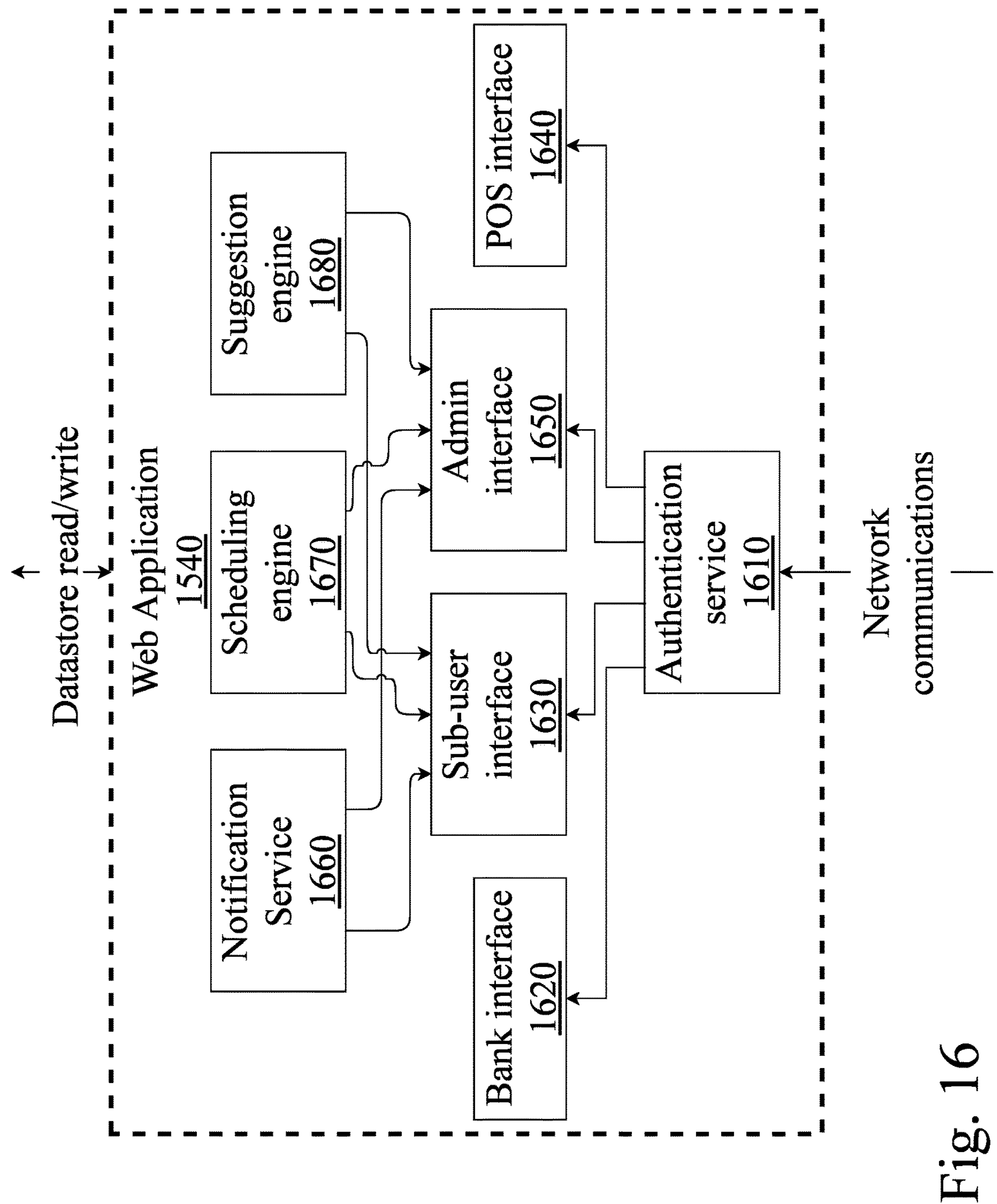
FIG. 16 is a system diagram of a web application used for third-party food and dining and retail purchase ordering control, according to an embodiment.

FIG. 16 is a system diagram of a web application used for third-party food and dining and retail purchase ordering control, according to an embodiment. The web application 1540 encompasses or includes several services and interfaces for operation, including an authentication service 1610, bank interface 1620, sub-user interface 1630, POS interface 1640, admin interface 1650, notification service 1660, scheduling engine 1670, and suggestion engine 1680. An authentication service 1610 may operate by unencrypting received data from another source such as a computer or mobile device communicating over HTTP or TCP protocols, or potentially some other protocol, and communicate with a datastore to determine if a received user authentication request is valid. For instance, user authentication requests may comprise encrypted username and password combinations that must then be checked against what is stored, or biometric information such as retinal scans, facial scans, voice data, or other biometrics. Authentication data is a one-to-many check in most cases, wherein user data is submitted and then compared to any entries in the datastore to locate a match, and if none are found, return a false identification result. If any matches are found, such as a matching username and password or matching biometrics to what is stored for a stored user, the requesting user and device may be logged into the application, and be presented with an interface to access the application further, such as a sub-user interface 1630 or administrator interface 1650. A bank interface 1620 is a non-graphical interface for financial institutions, which allows depositing of funds such as with debit card, bank account number and routing number, PAYPAL™ account information, or other financial data, through a secure channel and protocol such as HTTPS protocol. Sub-user interface 1630 and administrator interface 1650 may both be graphical user interfaces ("GUI") to display to specific types of users. A parent that is using the web application to deposit funds and control what their dependent may order with the deposited funds, for instance, would register with the application as an administrator, and then specify their dependent or dependents as sub-users that may log in with specific criteria that is either set by the parent or set by the dependent. A sub-user may register for an independent account as an administrator, but will not have access to the funds deposited by their caretaker or parent, thus defeating the purpose of utilizing the application for themselves, as they would only be able to deposit funds for their own account, rather than use the funds deposited by their caretaker for their use in authorized transactions. A POS interface 1640 is an interface, similarly, for communications from a point-of-sale system at a retailer or restaurant, that may communicate with the web application to determine if a specified user (authenticated with the authentication service) is able to purchase the specified goods for the specified price. If they have not enough funds, or are not permitted to purchase the specified goods from the specified vendor, they may be rejected, and the transaction cancelled. Otherwise, the funds may be withdrawn from the account, and transferred to the POS system.

Administrator interface 1650 may provide a graphical interface to specify notifications, scheduling, and suggestions, with their respective services in the application 1660, 1670, 1680, wherein the notifications comprise at least an option to have notifications sent to a third party including the owner of the administrator account for any attempts at withdrawing funds for purchases from a sub-user, or by the administrator themselves, such as with email notifications, SMS notifications, or notifying an account with the web application such that upon logging in, they see the specified notification. An example of such a notification may be an email sent to a parent, "2020-05-24 JOHN DOE attempted to purchase 'MACARONI AND CHEESE' from vendor 'WAL-MART OF LOS ANGELES' for $8.00," or something similar to a doctor, if an account has been set up to notify a doctor of purchases made, in keeping with dietary restrictions placed on the account. Scheduling may be set up with a scheduling engine 1670 such that specific purchases, and specific vendors or classes of vendors, may only be purchased or purchased from, on a specific schedule, such as only allowing alcohol to be purchased once every month, or only allowing foods from restaurants to be purchased once a week, allowing an administrator to control certain aspects of budgeting and lifestyle choices made with the deposited funds for sub-users. The suggestion engine 1680 may be used within the app to provide suggestions of foods, recipes, local restaurants or grocery stores, that may interest a user or sub-user based on specified interests and preferences, such as preferences for dairy foods, spicy foods, or specific types of restaurants such as Mexican restaurants within 10 miles. Sub-users may set their own suggestions preferences if permitted by the administrator, and their actions with the deposited funds from the administrator are restricted based on the scheduling engine, restriction settings from the administrator, and notifications may be sent out upon attempting to use the deposited funds, based on the settings specified by the administrator, if any, using for instance, email notifications, SMS notifications, or notifications seen on log-in of an account.

Detailed Description of Exemplary Aspects

Figure 4:
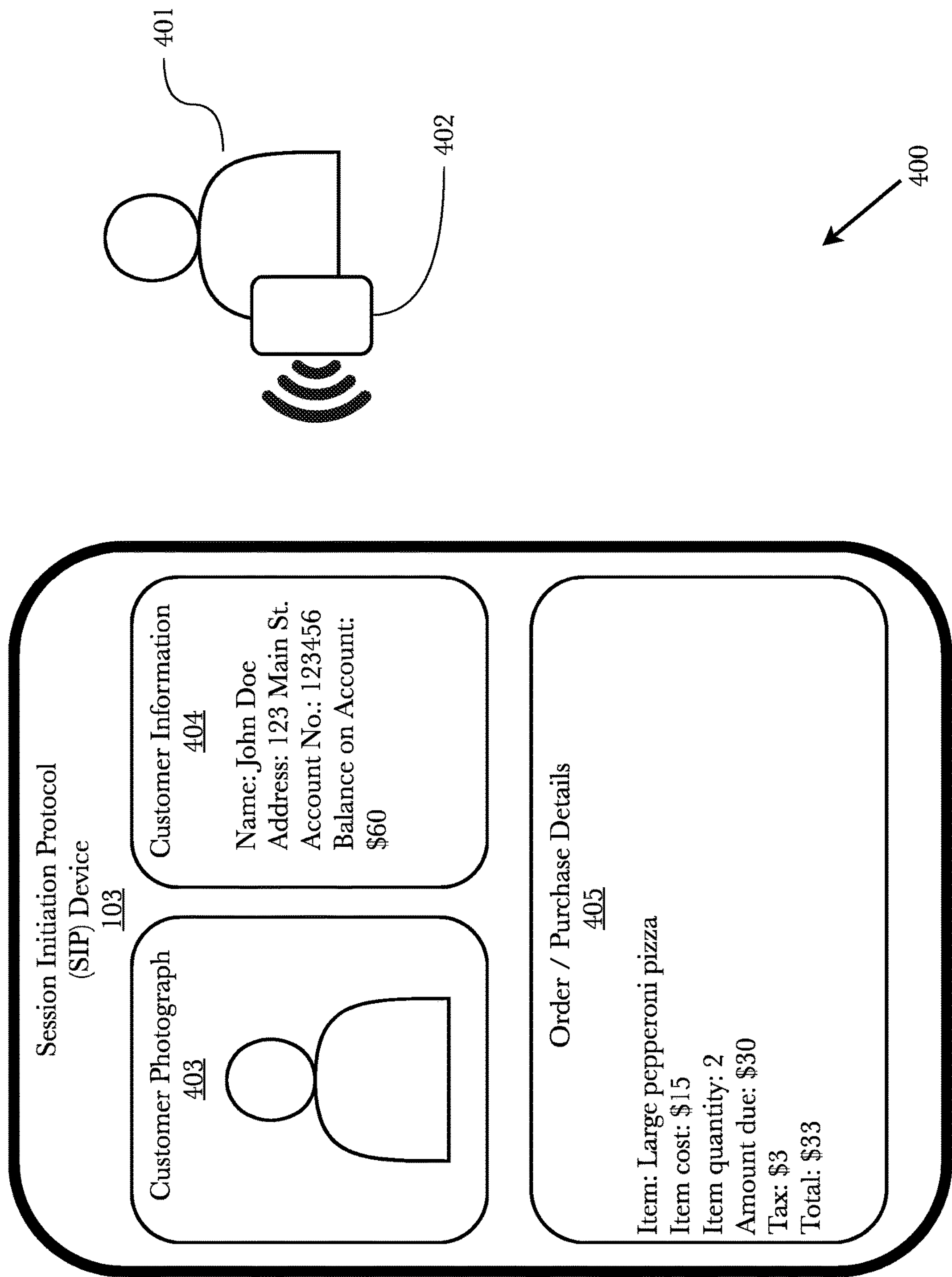
FIG. 4 is a diagram illustrating an exemplary business/customer interaction and showing an exemplary screenshot.

FIG. 4 is a diagram illustrating an exemplary business/customer interaction 400 and showing an exemplary screenshot. In this example, a customer 401 (who already has an account and registered device 402 at a business establishment) makes an order. The customer's device 402 and the payment facilitation device 103 detect each other and establish a connection when the customer 401 enters the business establishment. The customer's photograph 403 is displayed on the business' payment facilitation device 103, along with the customer's information 404 and order details 405. An employee of the business clicks on the customer photograph 403 to confirm the identity of the customer 401. Once confirmed, the customer device 402 automatically approves payment and receives confirmation of the payment without the customer having the handle the device 402. The customer device 402 may remain in the customer's pocket, purse, backpack, etc., and does not have to be removed to complete the transaction.

Figure 5:
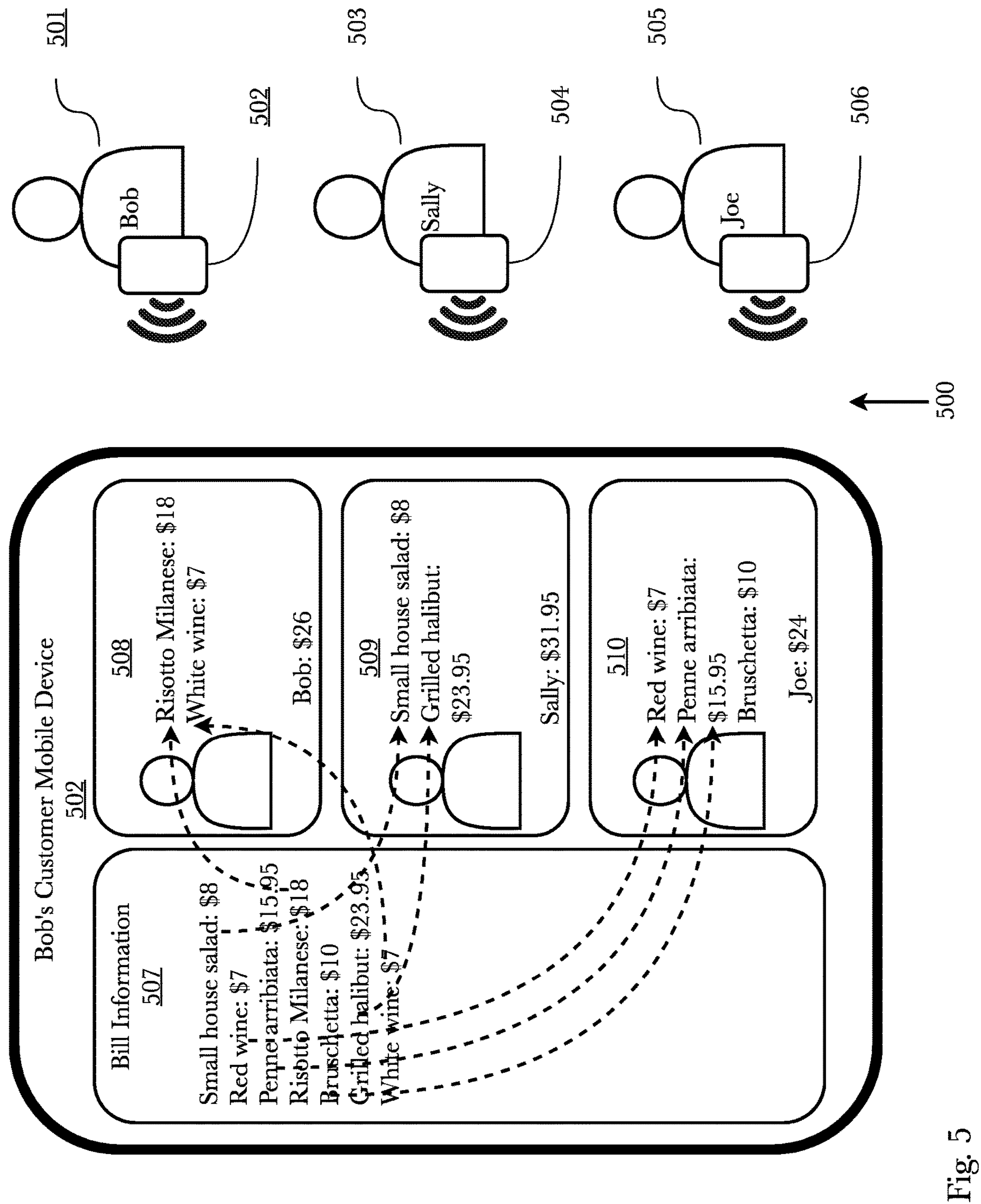
FIG. 5 is a diagram illustrating an exemplary bill splitting feature and showing an exemplary screenshot.

FIG. 5 is a diagram illustrating an exemplary bill splitting feature 500 and showing an exemplary screenshot. In this example, three customers, Bob 501, Sally 503, and Joe 505, each with their respective mobile devices 502, 504, and 506, have a meal together at a restaurant and want to split the bill among themselves. Each customer's mobile device has a bill splitting application installed on it, which shows a copy of the bill and the customers who dined together. For example, Bob's 501 mobile device 502 shows the bill information 507 for the group on the left-hand side of his screen, and a window for himself 508, a window for Sally 509, and window for Joe 510 on the right side. The mobile devices 504, 506 of Sally 503 and Joe 505 show similar screens. The windows 508, 509, 510, each show a photo (or other representation) of the customer, a space for allocating items from the bill, and a total of the items allocated to that customer. As each customer, on his or her respective mobile device 502, 504, 506, allocates food and drink items from the bill information 507 by clicking on them and dragging them to the window of a person on the right, the allocation of those food and drink items appears in the window of the person to whom the item has been allocated, as indicated by the arrows. For example, the risotto Milanese and white wine have been allocated to Bob (either by Bob or by one of the other two customers), a total due from Bob of $26 is shown, and this information is updated on all three mobile devices 502, 504, 506. Once all three customers 501, 503, 505 approve the allocation, each person's mobile device 502, 504, 506 processes the payment for the amount allocated to that customer. In some embodiments, unallocated items may be automatically split among the customers in the group.

Figure 6:
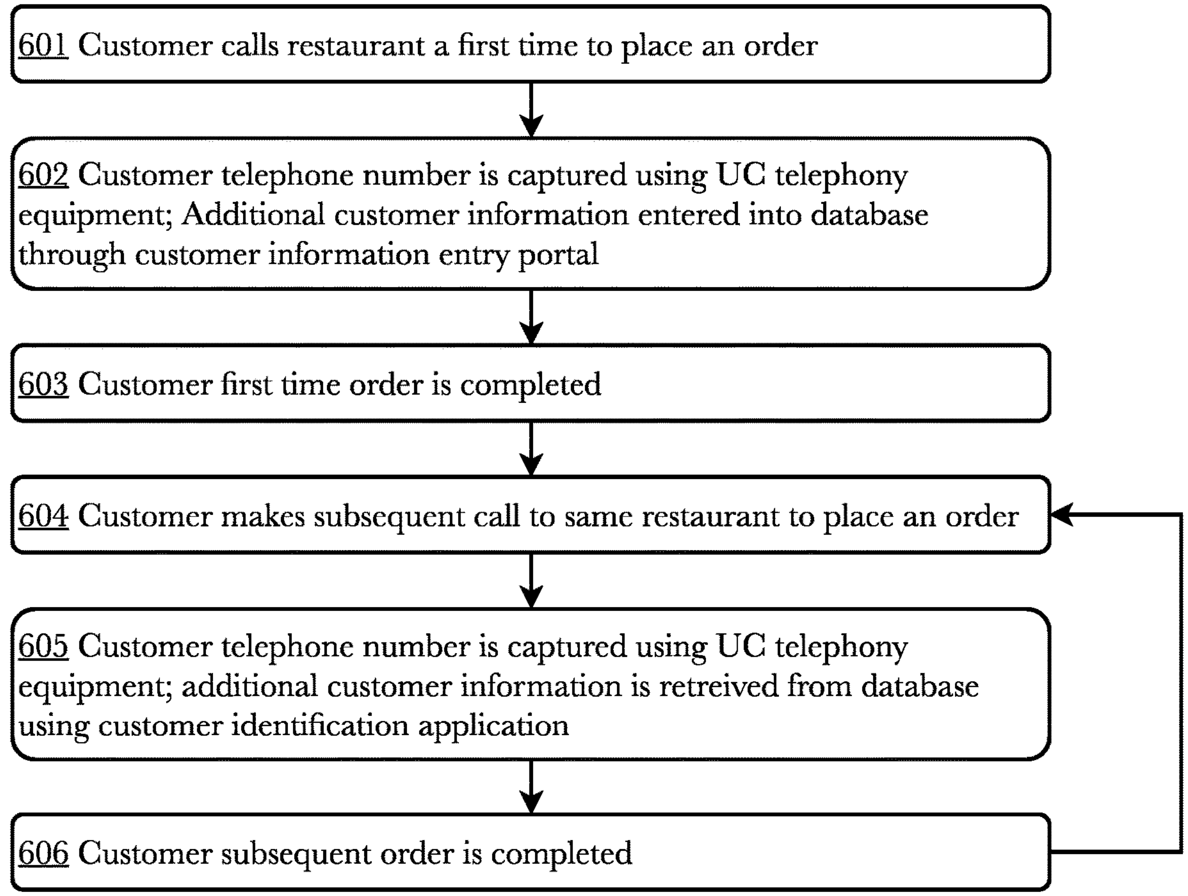
FIG. 6 is a flow diagram showing the steps of an exemplary method for registration of a customer's mobile device and order placement.

FIG. 6 is a flow diagram showing the steps of an exemplary method for registration of a customer's mobile device and order placement. When a customer calls a restaurant a first time to place an order 601, the customer's telephone number is captured using UC telephony equipment, and additional customer information is gathered and entered into database by an employee of the business 602. The customer then makes his or her order and the order is completed 603. Each time the customer makes a subsequent call to same business to place an order 604, the customer's telephone number is captured using UC telephone equipment, and the customer's information is retrieved from a customer database using a customer identification application 605. The customer than makes his or her order and the order is completed 606 without the customer having to provide his or her information. The same procedure is used when a customer physically enters a business establishment, except that the registration is performed in person.

Figure 7:
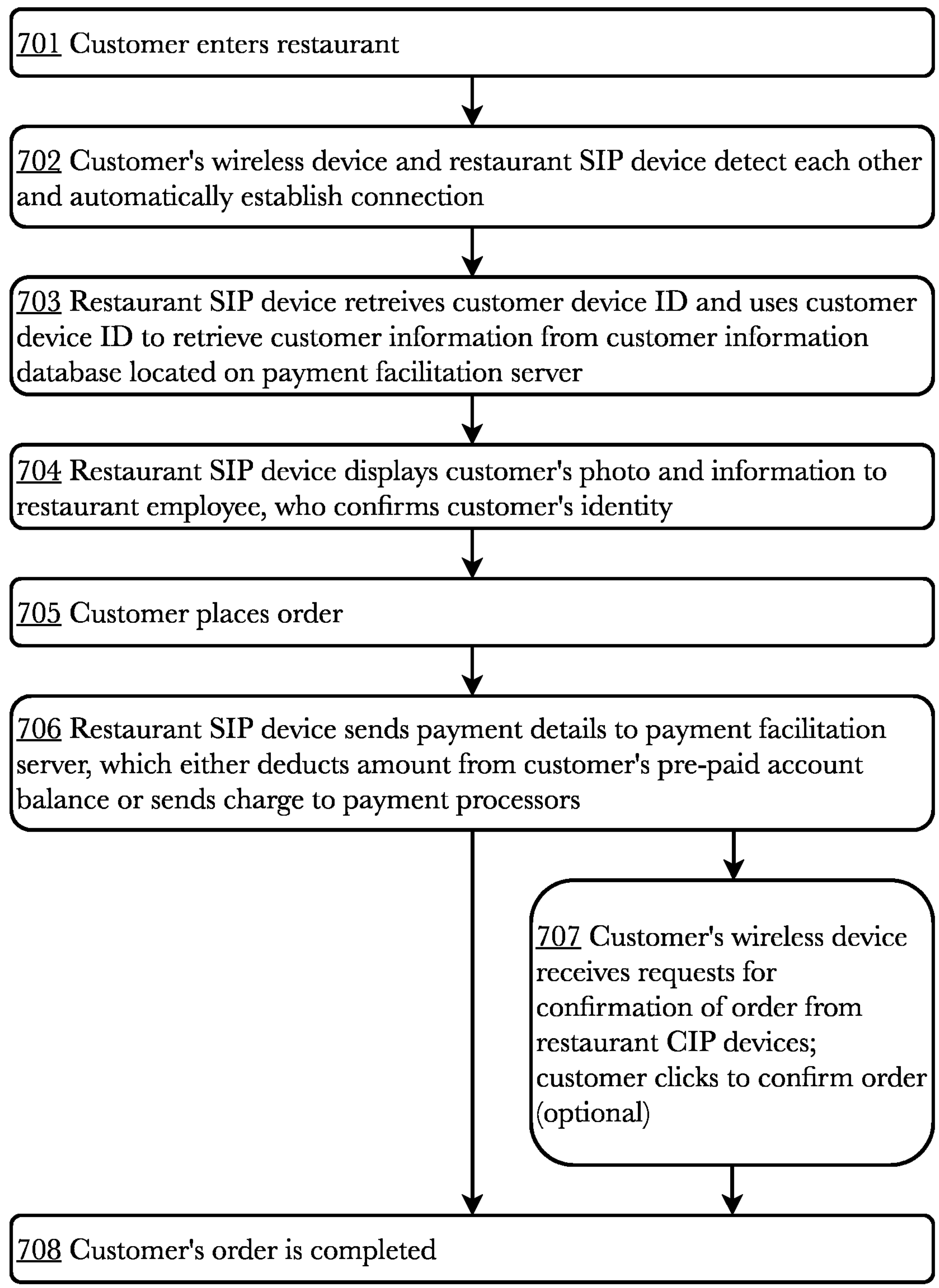
FIG. 7 is a flow diagram showing the steps of an exemplary method for zero-step authentication and completion of a transaction.

FIG. 7 is a flow diagram showing the steps of an exemplary method for zero-step authentication and completion of a transaction. When a customer enters a business establishment 701, the customer's wireless device and business payment facilitation device detect each other and automatically establish connection 702. The business payment facilitation device retrieves the customer device identifier (ID) and uses the customer device ID to retrieve customer information from customer information database located on a payment facilitation server 703. The business payment facilitation device displays customer's photo and information to a restaurant employee, who confirms customer's identity by clicking on the photo of the customer 704. The customer then places an order 705. When the order is placed, the business payment facilitation device sends payment details to payment facilitation server, which either deducts amount from customer's pre-paid account balance or sends charge to payment processors 706. Optionally, an additional security step may be inserted wherein the customer's wireless device receives and displays a request for confirmation of the order from the business CIP device and the customer clicks on the displayed request to confirm the order 707. Finally, the customer's order is completed 708.

Figure 8:
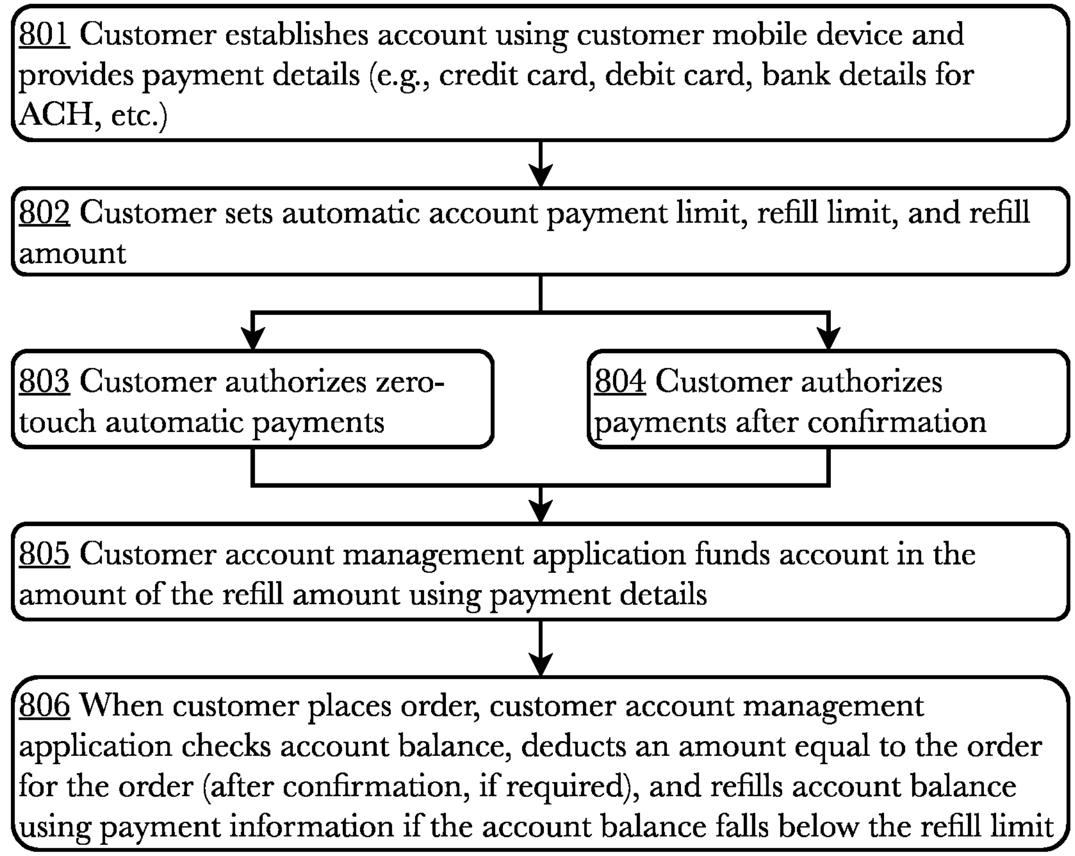
FIG. 8 is a flow diagram showing the steps of an exemplary method for establishment of an account and pre-authorization of payments.

FIG. 8 is a flow diagram showing the steps of an exemplary method for establishment of an account and pre-authorization of payments. First, a customer establishes an account using his or her customer mobile device and provides payment details (e.g., credit card, debit card, bank details for ACH, etc.) 801. The customer then sets an automatic account payment limit, a refill limit, and a refill amount 802. For example, the customer may set a payment limit for each transaction at $50, a refill limit (i.e., minimum account balance below which the account will be automatically refilled) of $10, and a refill amount of $100. The customer may choose to have such payments sent automatically without handling his or her mobile device (zero-step authentication) 803 or may choose to authorize each payment individually using his or her mobile device 804. A customer account management application funds the account in the amount of the refill amount using payment details 805. Thus, in this example, the customer has pre-authorized payments of up to $50 per transaction, and pre-authorized the system to automatically refill his account from the customer's financial institution (or credit card) in the amount of $100 whenever the account balance falls below $10. When the customer places an order, the customer account management application checks account balance, deducts an amount equal to the amount for the order (after confirmation, if required), and refills account balance using payment information if the account balance falls below the refill limit 806.

FIG. 9 is a flow diagram showing the steps of an exemplary method for bill splitting among customers. Each customer mobile device runs an application that shows nearby customer devices also using the payment system 901. Customers dining together form a group by selecting one another (or accepting a group formation created by one or more of them) 902. Each customer's device displays a copy of the itemized bill on one side of the screen, and a photo (or other representational image) of each other customer in the group on the other side of the screen 903. One or more of the customers in the group assigns payment by clicking and dragging items from the itemized bill to the photo (or image) of the customer responsible for paying for that item 904. When the group is finished assigning payments, each customer approves his/her proposed payment assignments, with unassigned items being distributed equally among the customers in the group 905. After all customers in the group have approved their payment assignments, the payment system processes payments from each customer's account according to the approved payment assignments 906.

Figure 10:
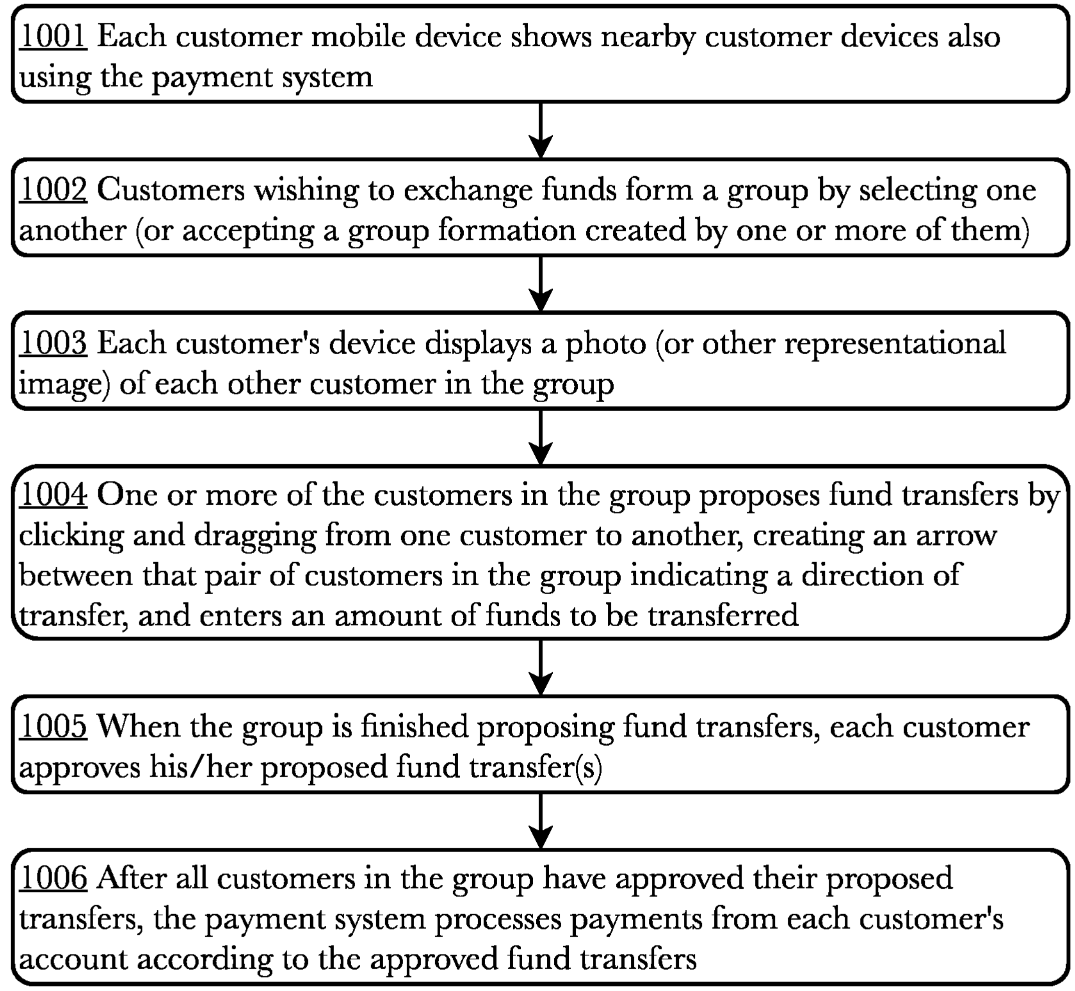
FIG. 10 is a flow diagram showing the steps of an exemplary method for funds transfer among customers.

FIG. 10 is a flow diagram showing the steps of an exemplary method for funds transfer among customers. Each customer mobile device runs an application that shows nearby customer devices also using the payment system 1001. Customers wishing to exchange funds form a group by selecting one another (or accepting a group formation created by one or more of them) 1002. Each customer's device displays a photo (or other representational image) of each other customer in the group 1003. One or more of the customers in the group proposes a fund transfer by clicking and dragging from one customer to another, creating an arrow between that pair of customers in the group indicating a direction of transfer, and enters an amount of funds to be transferred 1004. When the group is finished proposing fund transfers, each customer approves his/her proposed fund transfer(s) 1005. After all customers in the group have approved their proposed transfers, the payment system processes payments from each customer's account according to the approved fund transfers 1006.

Figure 17:
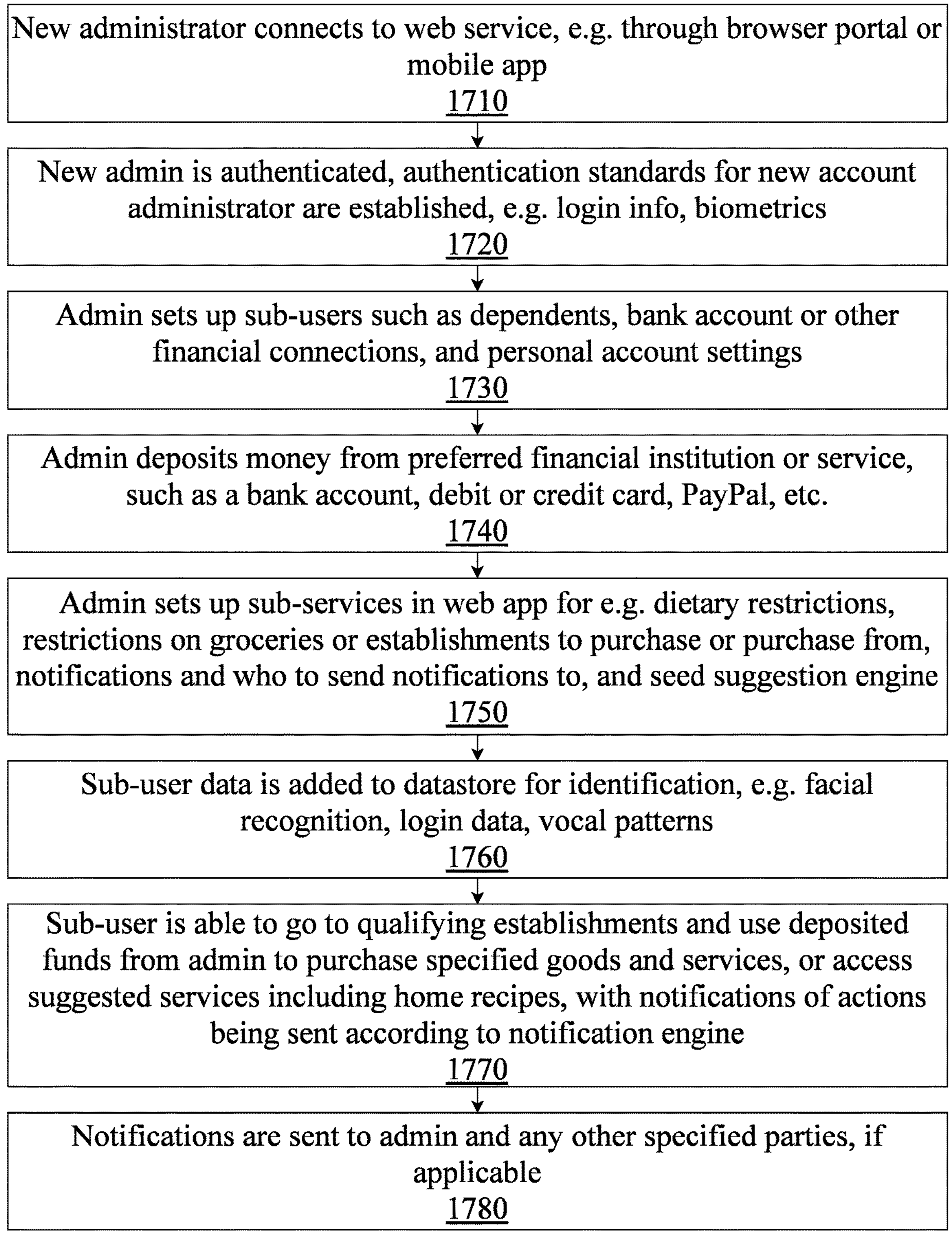
FIG. 17 is a method diagram illustrating the function of a system for third-party food and dining and retail purchase ordering control, according to an embodiment.

FIG. 17 is a method diagram illustrating the function of a system for third-party food and dining and retail purchase ordering control, according to an embodiment. Upon first attempting to use the system and the application therein, a new administrator may connect to the application or web service, through either a web browser such as GOOGLE CHROME™, MICROSOFT EDGE™, SAFARI™, or other web browsers, or it may be connected to and accessed with a specific application 1710 such as a mobile application on a phone, or a desktop application on a personal computer including laptops and some forms of tablet computers. Upon connecting to the web application, the new admin must establish authentication standards for their new account, such as either or a combination of login information, a pairing with a mobile device, or biometrics 1720. Login information may comprise at least a username and password combination, while biometrics may be voice patterns discerned through a microphone recording, facial scanning through the submission of a photo of the user's face, fingerprint scanning, retinal scanning, or other forms of biometrics if desired, or pairing of a specific mobile device which may be recognized upon attempting to pay with the device at an establishment. Login information may then be encrypted and stored in a datastore, for later use. An administrator may then set up sub-users such as dependents, set up bank account or other financial institution connections such as PAYPAL™, and personal account settings 1730. These settings may include contact information, username and password changing, notification settings, scheduling settings, sub-user settings, and more, which may be specified using a graphical user interface with, for instance, drop-down menus, text menus, and other elements common for GUI's to allow users to specify settings and preferences. The admin then may deposit money from their preferred financial institution or service, such as a bank account, debit or credit card, PAYPAL™, or other financial institutions or services 1740. The admin may set up sub-services in the web application, for instance dietary restrictions, restrictions on groceries or establishments to purchase or purchase from, notifications and who to send notifications to, and may also seed the suggestion engine 1750 with examples of their interests, classes of objects, foods, restaurants, and styles that interest them, and more. A suggestion engine may be seeded with examples of restaurant, food, or grocery store types or categories, examples of specific establishments or recipes, and then the application may be used to suggest similar establishments or recipes to users when queried. Sub-user data may then be added by the administrator, and subsequently saved to the datastore for identification, in a similar manner to the administrator's own login information 1760. This login information for a sub-user such as a dependent, or a doctor's patient, may include a username and password, or biometric information for authentication, or a combination of both. Biometrics that may be utilized include but may not be limited to facial recognition, retinal scanning, and vocal patterns 1760. As part of the account setup, administrators may also deposit funds from their connected financial institutions, to be used either by themselves or by any sub-users they have set up in their account. A potential sub-user is then able to go to qualifying establishments and use any deposited funds from the administrator to purchase permitted goods and services, or access suggested services including home recipes, with notifications of actions being sent according to notification engine 1770. Purchasing such goods from businesses may be done with zero-step authentication at the premises, such as passively matching their face upon entry into the business or their vocal patterns in a similar manner once they speak to a host or cashier, or they may log in with a swipe of an ID card, or a username and password, or some other method. Upon any attempts at using the deposited funds by a sub-user or even by the administrator as the case may be, notifications may be sent to the admin or to any other specified parties, if applicable 1780. For instance, an email notification may be sent to a doctor that the administrator is purchasing certain foods, to alert the doctor of any dietary changes for the patient. Parents may also receive notifications this way about their children purchasing anything in this way, even if the attempt at purchasing is unsuccessful.

Figure 18:
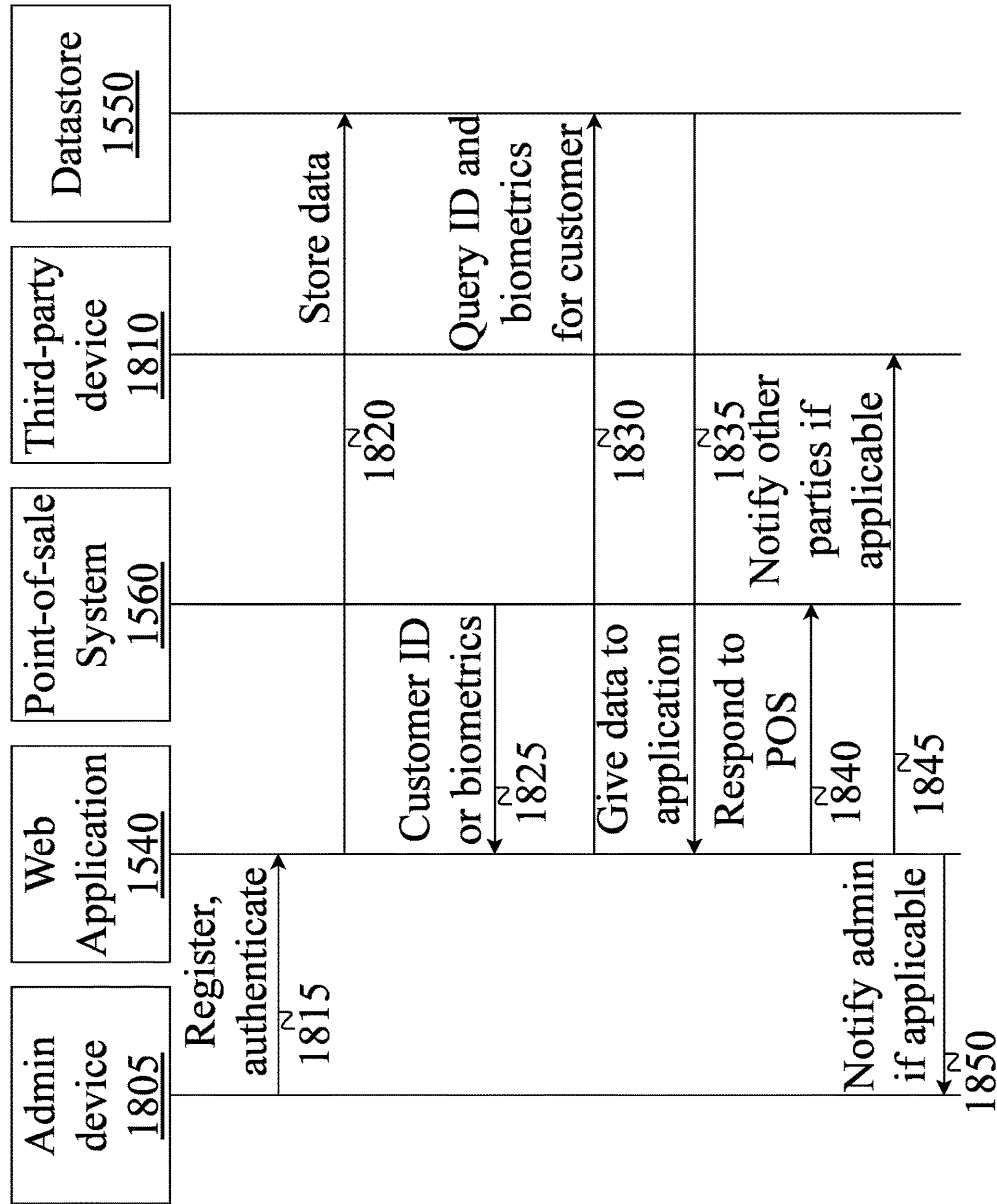
FIG. 18 is a message flow diagram illustrating the use of a system for third-party food and dining and retail purchase ordering control, according to an embodiment.

FIG. 18 is a message flow diagram illustrating the use of a system for third-party food and dining and retail purchase ordering control, according to an embodiment. Devices exchanging messages and data include an admin device 1805, which may be a mobile device including a phone or tablet, or a personal computer such as a laptop or desktop, a web application 1540 operating on a server accessible over the Internet, a POS system 1560 at a restaurant or store which may communicate over the internet with the web application 1540, a third party device 1810 such as a mobile device or personal computer which may be used by a third party for the purpose of receiving notifications such as emails, SMS messages, or logging into the web application 1540 to view notifications manually, and a datastore 1550 that may store data for a web application 1540 such as user authentication and user settings. A datastore 1550 may be a SQL database, a non-SQL based database, or other data storing and querying solutions. An admin device 1805 must send a registration and authentication 1815 message to the web application 1540. An authentication message may be encrypted and then decrypted using matching software and encryption techniques at the endpoint, and may be sent over one of several protocols and methodologies, including using secure API calls in an application, using encrypted POST-GET methods using HTTP, sending data packets directly to an awaiting socket on the destination server, or another method. Then the web application sends the data to a datastore 1550 for storage 1820. Such a datastore may be a SQL database such as MYSQL™, it may be a non-SQL database such as MONGODB™, it may be managed or unmanaged, or it may even be a non-database datastore, such as a data file or some other method of storing data. A point-of-sale system 1560 then may receive data on a customer attempting to make a purchase, and sends the customer ID, login information, mobile device ID, or biometrics to the web application 1540 for identification and authentication 1825. The customer ID, login information, or biometrics are then queried in the datastore 1550 by the web application 1540, 1830. Such an attempt at identifying a user is a one-to-multiple check where a single identifying piece of data, or a few identifying pieces of data taken in concert, are compared to multiple records to locate the matching records of interest, which in this case are likely to be a user and their matching permissions and restrictions and funding. These requests may be sent over a variety of protocols over a variety of networks, including HTTP with POST-GET methods, API calls, communicating over a local or wide area network, communicating over the Internet, or other common networking solutions for communicating with a datastore for authenticating users. The datastore 1550 responds with the customer data, if any, to the web application 1540, 1835, in the case of a successful or unsuccessful authentication. An unsuccessful authentication request in this context may refer to a lack of matching data in the datastore compared to the received identifying information, whether due to a lack of such a user in the datastore, a mismatched piece of information supplied by the user, corruption in the data stream either going to or from the datastore or web application, unavailability of the datastore or data in question, and other common sources of issues with authenticating users. In this context, the web application's response in the event of an unsuccessful authentication may or may not discriminate between various reasons with the authentication failed. A failed authentication may also be the result of a lack of funds compared to what the POS has requested, indicating that even though the user may have been identified, they cannot complete the purchase as requested. The web application 1540 responds to the POS system 1560, 1840, with the successful or unsuccessful user authentication and funds, indicating whether or not the user may complete the transaction or not. Upon transaction success or failure 1840, the web application may notify a third party 1845 if applicable, and notify the administrator or administrators, if applicable 1850. Notifications may be accomplished through a variety of means and networks, including the Internet, phone networks such as a PSTN, SMS messaging, setting a notification flag for the user to read when they next log into the web application, or other notification methods common in the art for web applications to communicate with users.

Figure 19:
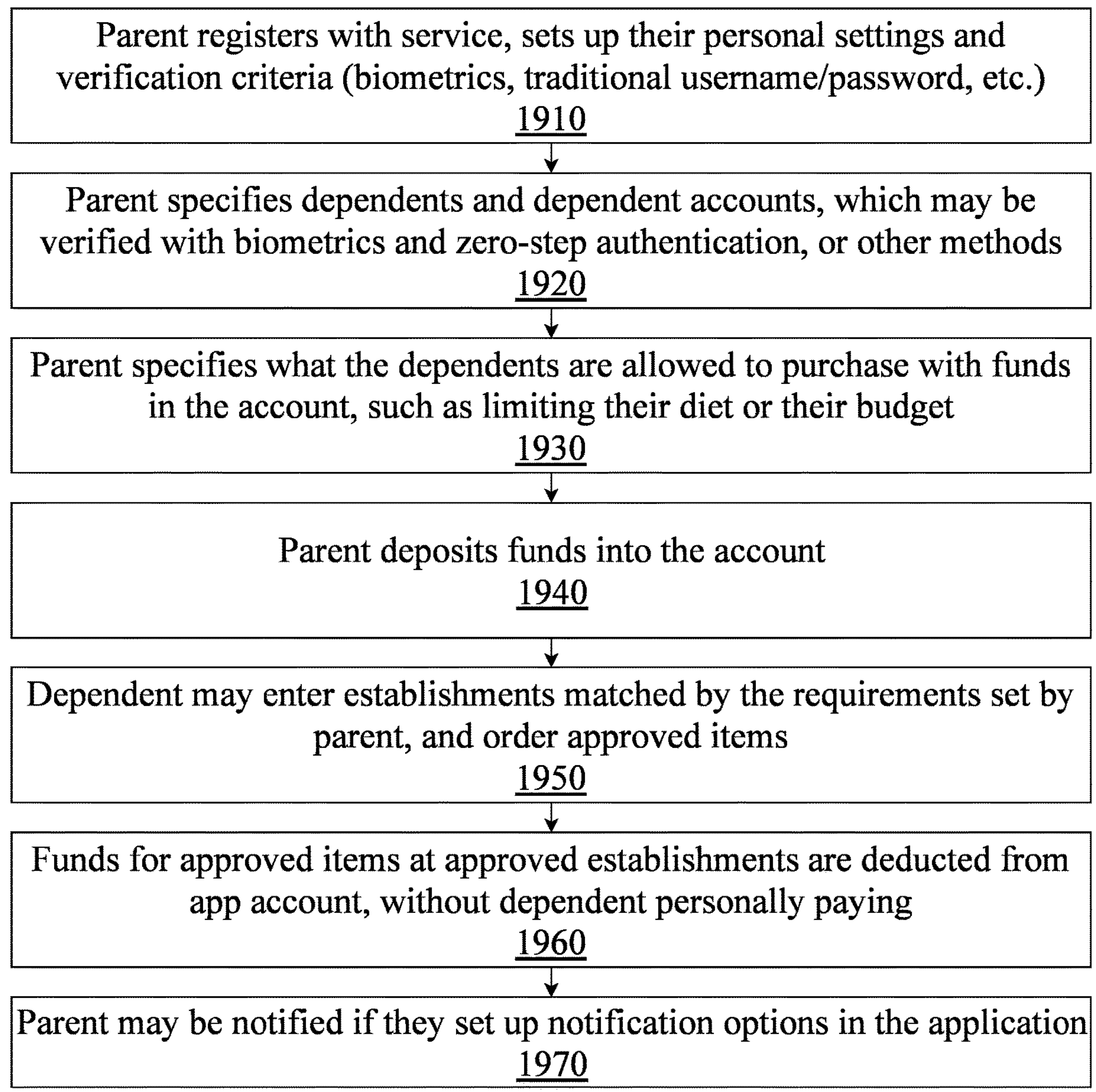
FIG. 19 is a method diagram illustrating the use of a system for third-party food, dining, and retail purchase ordering control, being used for a parent to monitor and control what a child or other dependent may order with deposited funds.

FIG. 19 is a method diagram illustrating the use of a system for third-party food, dining, and retail purchase ordering control, being used for a parent to monitor and control what a child or other dependent may order with deposited funds. A parent or caretaker such as a legal guardian may register an account with a web application, setting up their personal settings and verification criteria such as biometrics, a username and password, pairing a mobile device to then use at the point of sale for identification, or other identification criteria 1910. A parent or other caretaker then may specify dependents and dependent accounts, such as children, which may be verified with biometrics, zero-step authentication, traditional logging in with a username and password, or other methods 1920. Such user verification may be encrypted or unencrypted during various portions of the transmission to the web application from the time the user provides the data, and may be sent using TCP protocol, HTTP protocol, UDP protocol, HTTPS protocol, or others. The parent or other admin then may specify what the dependents or other sub-users are allowed to purchase with funds in the account, such as limiting their diet or their budget 1930, before depositing funds into the account 1940. The sub-user or sub-users may enter establishments matched by the requirements set by parent, and order approved items 1950, and use the deposited funds for approved items at approved establishments are deducted from app account, without the sub-user personally paying 1960, and allowing the parent or other admin to be notified if they set up notification options in the application 1970 during the initial setup of their settings and preferences 1910.

Figure 20:
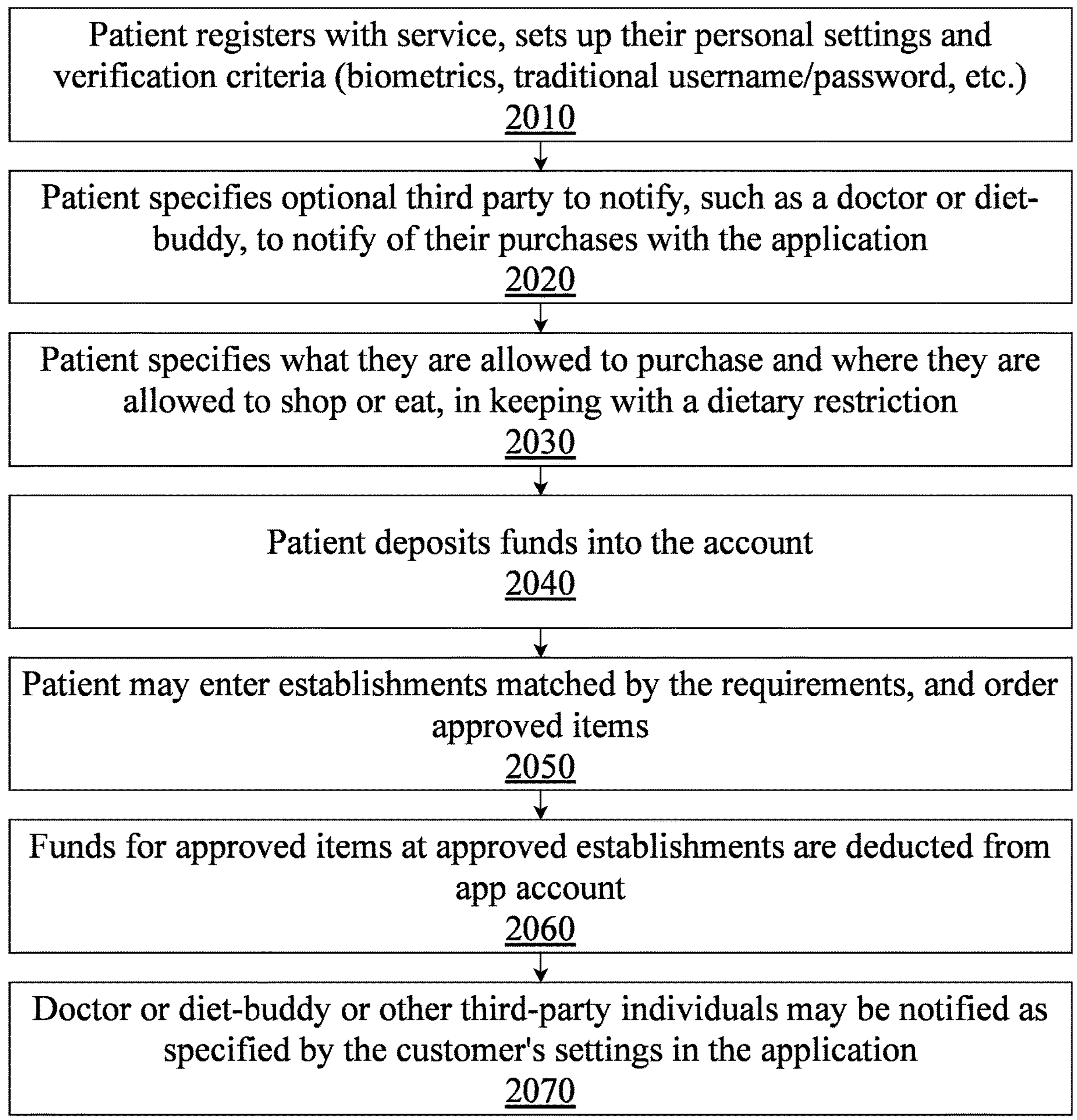
FIG. 20 is a method diagram illustrating the use of a system for third-party food, dining, and retail purchase ordering control, being used for a patient to monitor and control what they eat with self-reporting or reporting to a doctor or other third-party, potentially with a doctor dictating the dietary restrictions on the patient account.

FIG. 20 is a method diagram illustrating the use of a system for third-party food, dining, and retail purchase ordering control, being used for a patient to monitor and control what they eat with self-reporting or reporting to a doctor or other third-party, potentially with a doctor dictating the dietary restrictions on the patient account. A patient may register an account with a web application, setting up their personal settings and verification criteria such as biometrics, a username and password, pairing a mobile device to then use at the point of sale for identification, or other identification criteria 2010. Such user verification may be encrypted or unencrypted during various portions of the transmission to the web application from the time the user provides the data, and may be sent using TCP protocol, HTTP protocol, UDP protocol, HTTPS protocol, or others. The patient may specify a third party to notify, such as a doctor, dietician or friend who may be dieting with them or helping them keep track of their diet, to notify of their purchases with the application 2020. The patient may specify what they are allowed to purchase and where they are allowed to shop or eat, in keeping with a dietary restriction 2030, in the same manner of restrictions as in previous methods where an administrator prevents a sub-user from accessing funds for unauthorized purchases. It is possible for the patient to be an administrator and self-regulate their account, or to be a sub-user with a doctor or dietician as the administrator who regulates the account, with the user paying for the deposits into the account, and the administrator regulating what they can then use the deposited money for after the patient deposits funds into the account 2040. The patient or dieter may then enter establishments matched by the requirements, and order approved items 2050 if the funds in the account at least match the minimum required for the purchase, at which point the funds for the approved items at approved establishments are deducted from app account 2060. The doctor or diet-buddy or other third-party individual or individuals may be notified as specified by the customer's settings in the application 2070, either from the user's settings, or from the administrator settings if the two are not identical, as in the case of the doctor being the administrator and the patient being a sub-user.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 11:
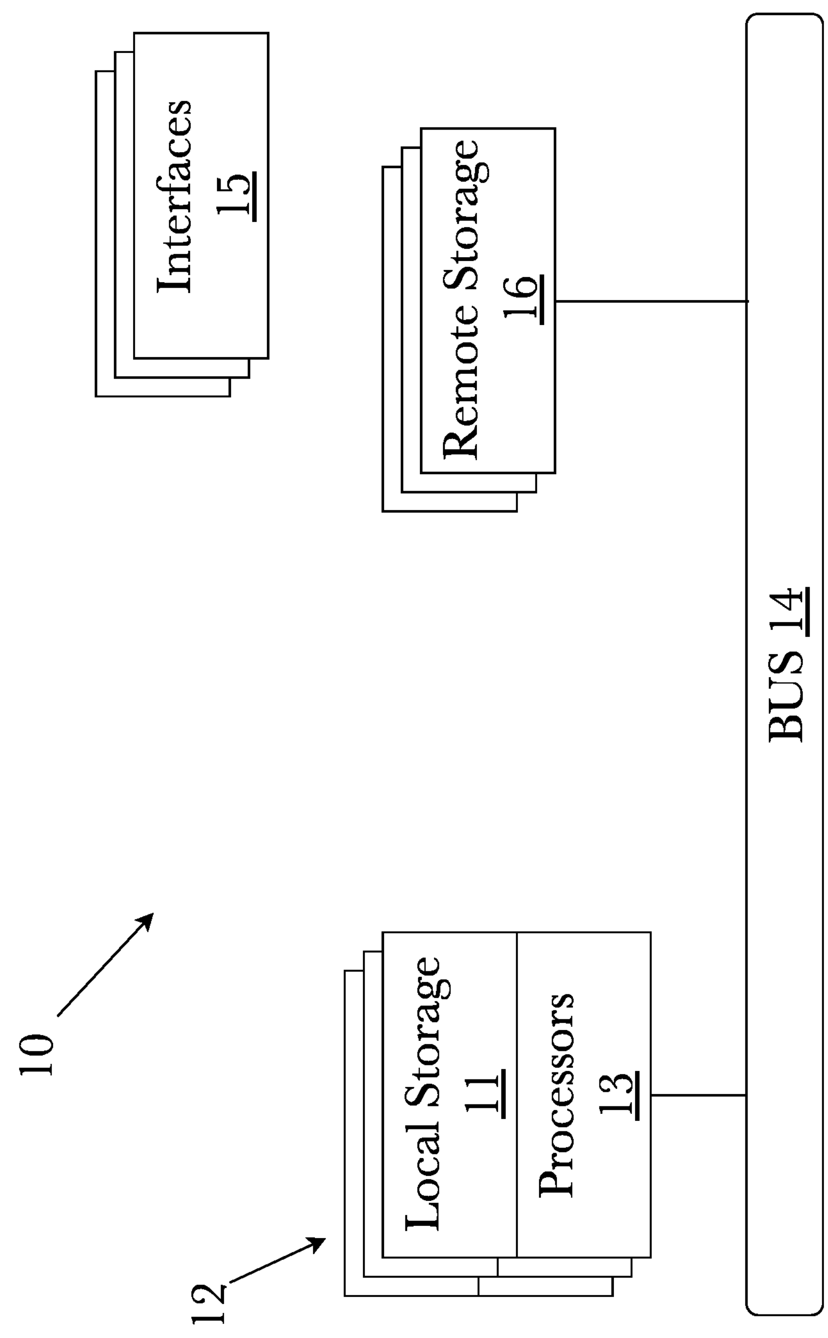
FIG. 11 is a block diagram illustrating an exemplary hardware architecture of a computing device.

Referring now to FIG. 11, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10. Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 11 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 12:
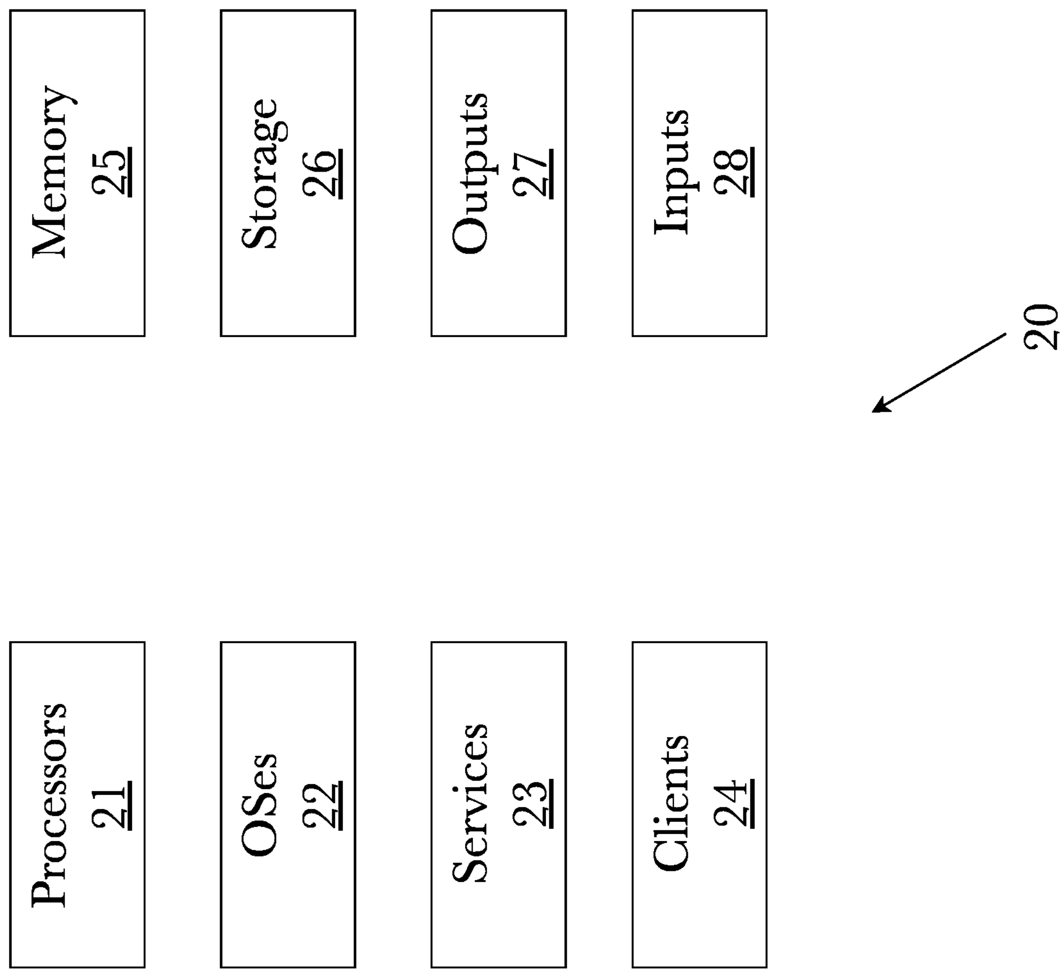
FIG. 12 is a block diagram illustrating an exemplary logical architecture for a client device.

In some aspects, systems may be implemented on a standalone computing system. Referring now to FIG. 12, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 11). Examples of storage devices 26 include flash memory, magnetic hard drive, CD-ROM, and/or the like.

Figure 13:
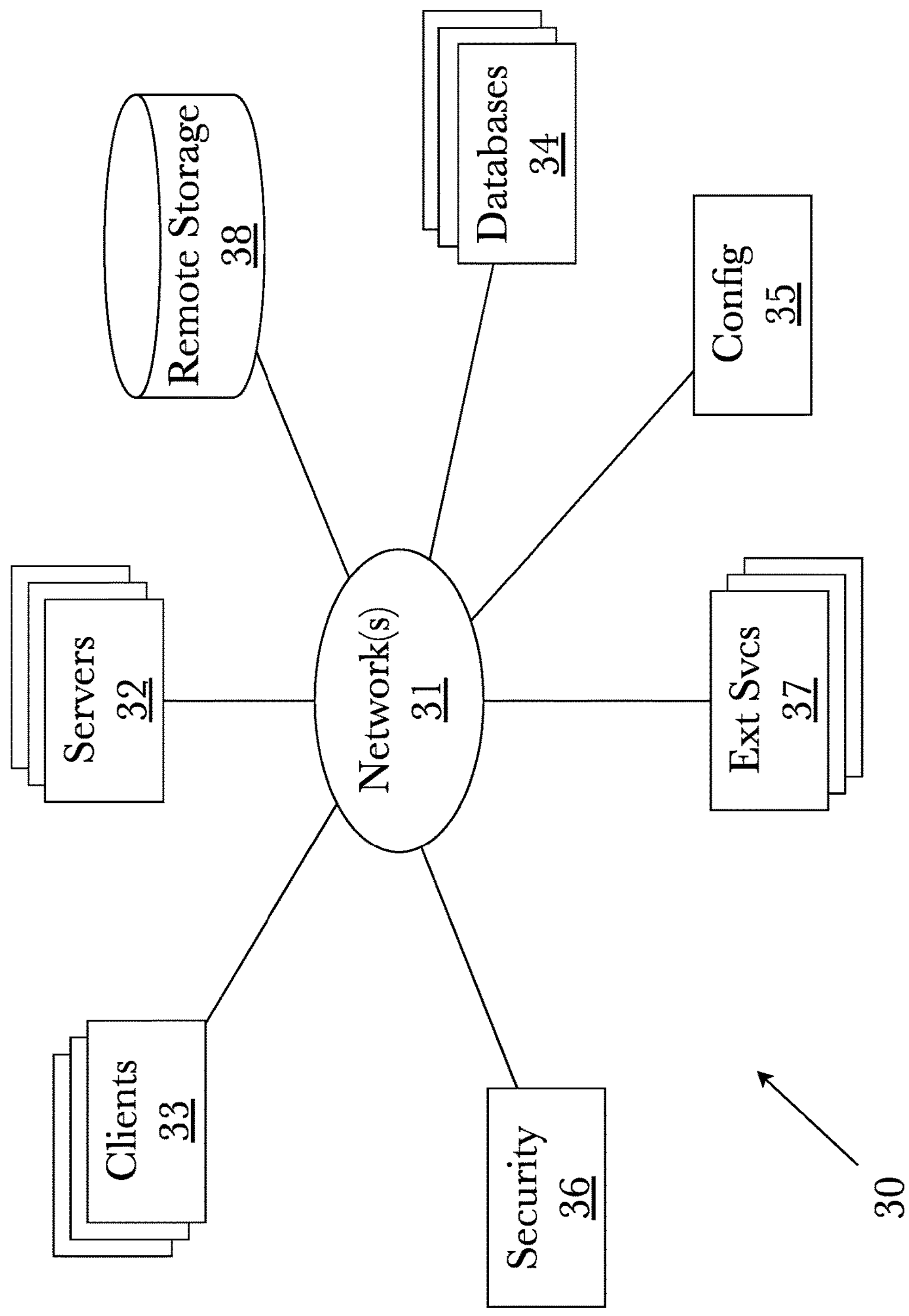
FIG. 13 is a block diagram showing an exemplary architectural arrangement of clients, servers, and external services.

In some aspects, systems may be implemented on a distributed computing network, such as one having any number of clients and/or servers. Referring now to FIG. 13, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 12. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 14:
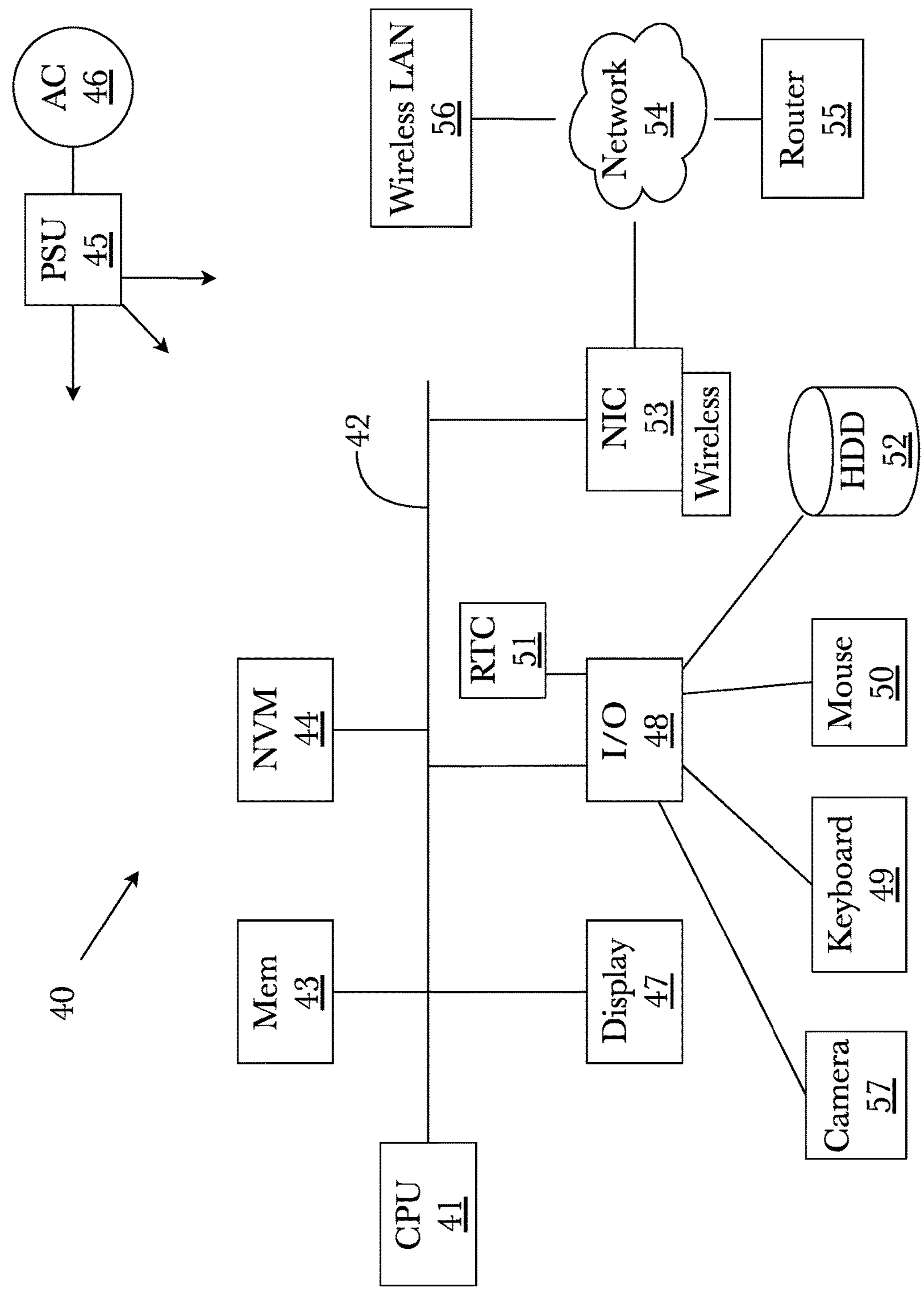
FIG. 14 is another block diagram illustrating an exemplary hardware architecture of a computing device.

FIG. 14 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for exercising third-party control over a first person's food and dining ordering, comprising:

a payment facilitation server comprising a first plurality of programming instructions stored in a memory of, and operating on a processor of, a first computing device, wherein the plurality of programming instructions, when operating on the processor, cause the first computing device to:

receive user account data for a registered user from a user device via a network;

receive a deposit request from the registered user;

process a funds transfer from the registered user's financial account to the user account;

associate a subordinate user with the registered user;

receive a merchant authorization from the registered user;

provide zero-step authorization wherein a subordinate user is automatically authorized to perform a transaction at a specific restaurant or retail location using funds associated with the registered user, the authorization comprising the steps of:

comparing of the restaurant or retail location against any available merchant authorizations for the subordinate user to determine whether the subordinate user is authorized to perform the transaction at the restaurant or retail location; and comparing any merchant authorizations against the registered user corresponding to the funds used in the transaction to determine whether the merchant authorization was provided by the registered user;

permit the transaction using the funds corresponding to the registered user to process only if the subordinate user is authorized via the zero-step authentication; and transmit a notification over the network to the registered user based on the attempted transaction; and a payment facilitation device comprising a second plurality of programming instructions stored in a memory of, and operating on a processor of, the payment facilitation device, wherein the second plurality of programming instructions, when operating on the processor of the payment facilitation device, cause the payment facilitation device to:

detect a wireless mobile device registered to the subordinate user;

establish a wireless connection with the wireless mobile device;

obtain a device identifier for the wireless mobile device;

send the device identifier to the payment facilitation server;

receive customer information for the wireless mobile device from the payment facilitation server;

display a photograph of the user;

transmit transaction details to a mobile device of the registered user for approval;

receive authentication of the transaction details from the registered user mobile device; and send the transaction details to the payment facilitation server for processing of the transaction.

2. The system of claim 1, wherein the registered user and any specified subordinate users provide biometric information for the purpose of authentication with the system.

3. The system of claim 2, wherein the zero-step authorization uses the biometric data for authentication.

4. The system of claim 1, wherein the merchant authorization is based on patient dietary restrictions.

5. The system of claim 4, wherein the registered user is a guardian and the subordinate user is a dependent.

6. The system of claim 4, wherein the registered user is a medical professional and the subordinate user is a patient.

7. The system of claim 1, wherein the notification is transmitted via any one or combination of email, SMS messaging, or messages seen upon logging into a web application.

8. The system of claim 1, wherein the data received from the registered user may be encrypted.

9. The system of claim 1, wherein the deposit request comprises financial information necessary to deposit funds from the registered user's financial account.

10. The system of claim 1, wherein funds are associated with the registered user of the user account.

11. The system of claim 1, wherein the displayed photograph of the user is associated with the wireless mobile device for confirmation of the identity of the subordinate user.

12. The system of claim 1, wherein the transaction details comprise a transaction amount.

13. The system of claim 1, wherein the subordinate user may be authorized to use the funds.

14. The system of claim 1, wherein the merchant authorization comprises at least one merchant where the funds may be used to conduct a transaction.

15. A method for exercising third-party control over a first person's food and dining ordering, comprising the steps of:

receiving user account data for a registered user from a user device via a network;

receiving a deposit request from the registered user;

processing a funds transfer from the registered user's financial account to the user account;

associating a subordinate user with the registered user;

receiving a merchant authorization from the registered user;

providing zero-step authorization wherein a subordinate user is automatically authorized to perform a transaction at a specific restaurant or retail location using funds associated with the registered user, the authorization comprising the steps of:

comparing of the restaurant or retail location against any available merchant authorizations for the subordinate user to determine whether the subordinate user is authorized to perform the transaction at the restaurant or retail location; and comparing any merchant authorizations against the registered user corresponding to the funds used in the transaction to determine whether the merchant authorization was provided by the registered user;

permitting the transaction using the funds corresponding to the registered user to process only if the subordinate user is authorized via the zero-step authentication; and transmitting a notification over the network to the registered user based on the attempted transaction;

detecting a wireless mobile device registered to the subordinate user;

establishing a wireless connection with the wireless mobile device;

obtaining a device identifier for the wireless mobile device;

sending the device identifier to the payment facilitation server;

receiving customer information for the wireless mobile device from the payment facilitation server;

displaying a photograph of the user;

transmitting transaction details to a mobile device of the registered user for approval;

receiving authentication of the transaction details from the registered user mobile device; and sending the transaction details to the payment facilitation server for processing of the transaction.

16. The method of claim 15, wherein the registered user and any specified subordinate users provide biometric information for the purpose of authentication with the system.

17. The method of claim 16, wherein the zero-step authorization uses the biometric data for authentication.

18. The method of claim 15, wherein the merchant authorization is based on patient dietary restrictions.

19. The method of claim 18, wherein the registered user is a guardian and the subordinate user is a dependent.

20. The method of claim 18, wherein the registered user is a medical professional and the subordinate user is a patient.

* * * * *